US011918693B2

(12) United States Patent
Andrews et al.

(10) Patent No.: US 11,918,693 B2
(45) Date of Patent: Mar. 5, 2024

(54) IBUPROFEN AND ACETAMINOPHEN TABLET

(71) Applicant: GlaxoSmithKline Consumer Healthcare Holdings (US) LLC, Wilmington, DE (US)

(72) Inventors: Christine Drumheller Andrews, Warren, NJ (US); Kevin Scott Kinter, Warren, NJ (US); Bonny Rene Shaw, Warren, NJ (US); David Ellis Kellstein, Warren, NJ (US)

(73) Assignee: HALEON US HOLDINGS LLC, Wilmington, DE (US)

( * ) Notice: Subject to any disclaimer, the term of this patent is extended or adjusted under 35 U.S.C. 154(b) by 380 days.

(21) Appl. No.: 16/910,485

(22) Filed: Jun. 24, 2020

(65) Prior Publication Data

US 2020/0405645 A1    Dec. 31, 2020

Related U.S. Application Data

(60) Provisional application No. 62/867,683, filed on Jun. 27, 2019.

(51) Int. Cl.
| | | |
|---|---|---|
| *A61K 9/20* | (2006.01) | |
| *A61K 9/28* | (2006.01) | |
| *A61K 31/167* | (2006.01) | |
| *A61K 31/192* | (2006.01) | |
| *A61K 9/00* | (2006.01) | |

(52) U.S. Cl.
CPC .......... *A61K 9/2866* (2013.01); *A61K 9/2009* (2013.01); *A61K 9/2018* (2013.01); *A61K 31/167* (2013.01); *A61K 31/192* (2013.01); *A61K 9/0053* (2013.01)

(58) Field of Classification Search
None
See application file for complete search history.

(56) References Cited

U.S. PATENT DOCUMENTS

| 4,757,090 | A | 7/1988 | Salpekar et al. | |
|---|---|---|---|---|
| 10,532,036 | B2 | 1/2020 | Atkinson | |
| 2019/0008781 | A1* | 1/2019 | Puckett | A61K 31/00 |
| 2019/0350883 | A1 | 11/2019 | Chau | |
| 2020/0268673 | A1* | 8/2020 | Murphy | A61K 9/145 |

FOREIGN PATENT DOCUMENTS

| PL | 195966 P1 | 11/2007 |
|---|---|---|
| WO | WO2007/034135 | 3/2007 |

OTHER PUBLICATIONS

Anderson BJ. Paracetamol (acetaminophen): mechanisms of action. Pacdiatr Anacsth 2008;18:915-921.
Athersuch TJ, Antoine DJ, Boobis AR, et al. Paracetamol metabolism, hepatotoxicity, biomarkers and therapeutic interventions: a perspective. Toxicol Res (Camb) 2018;7:347-357.
Beaver WT. Combination analgesics. Am J Med. 1984;77:38-53.
Becker DE. Pain management: Part 1: Managing acute and post-operative dental pain. Anesth Prog 2010;57:67-78; quiz 79-80.
Brain P, et al. Onset of analgesia and efficacy of ibuprofen sodium in postsurgical dental pain: a randomized, placebo-controlled study versus standard ibuprofen. Clin J Pain 2015;31:444-450.
Cooper SA, Schachtel BP, Goldman E, et al. Ibuprofen and acetaminophen in the relief of acute pain: a randomized, double-blind, placebo-controlled study. J Clin Pharmacol 1989;29:1026-1030.
Davies NM. Clinical pharmacokinetics of ibuprofen. The first 30 years. Clin Pharmacokinet 1998;34:101-154.
Dickman A. Choosing over-the-counter analgesics. Pharm J. 2008;281:631.
Doherty M, Hawkey C, Goulder M, et al. A randomised controlled trial of ibuprofen, paracetamol or a combination tablet of ibuprofen/paracetamol in community-derived people with knee pain. Ann Rheum Dis 2011;70:1534-1541.
Flower RJ and Vane JR. Inhibition of prostaglandin synthetase in brain explains the anti-pyretic activity of paracetamol (4-acetamidophenol). Nature 1972;240:4 1 0-411.
Goldman RD, Ko K, Linett LJ, Scolnik D. Antipyretic efficacy and safety of ibuprofen and acetaminophen in children. Ann Pharmacother. 2004;38:146-150. doi: 10.1345/aph.1C391.
Hersh EV, Levin LM, Cooper SA, et al. Ibuprofen liquigel for oral surgery pain. Clin Ther 2000;22:1306-1318.
Jaeschke H. Acetaminophen: dose-dependent drug hepatotoxicity and acute liver failure in 25 patients. Dig Dis 2015;33:464-471.
Kehlet H. Multimodal approach to control postoperative pathophysiology and rehabilitation. Br J Anaesth 1997;78:606-617.
Malya RR. Does combination treatment with ibuprofen and acetaminophen improve fever control? Ann Emerg Med. 2013;61:569-570. doi: 10.1016/j.annemergmed.2012.10.025.
Mehlisch DR, Aspley S, Daniels SE, et al. A single-tablet fixed-dose combination of racemic ibuprofen/paracetamol in the management of moderate to severe postoperative dental pain in adult and adolescent patients: a multicenter, two-stage, randomized, double-blind, parallel-group, placebo-controlled, factorial study. Clin Ther 2010;32:1033-1049.
Mehlisch DR, Aspley S, Daniels SE, et al. Comparison of the analgesic efficacy of concurrent ibuprofen and paracetamol with ibuprofen or paracetamol alone in the management of moderate to severe acute postoperative dental pain in adolescents and adults: a randomized, double-blind, placebo-controlled, parallel-group, single-dose, two-center, modified factorial study. Clin Ther 2010;32:882-895.

(Continued)

*Primary Examiner* — Susan T Tran

(57) ABSTRACT

The present invention provides novel compositions, methods of treatment and methods of manufacture of large scale, commercially viable ibuprofen and acetaminophen tablets. The unique characteristics and synergistic effects resulting from the disclosed compositions, methods of treatment and methods of manufacture demonstrate a product with optimal analgesia, anti-pyresis, safety profiles and large-scale manufacturability. The inventions described herein surprisingly show the unique composition and method of manufacturing for a large-scale commercial batch of a novel ibuprofen and acetaminophen tablet.

24 Claims, 12 Drawing Sheets

(56) References Cited

OTHER PUBLICATIONS

Mehlisch DR. The efficacy of combination analgesic therapy in relieving dental pain. J Am Dent Assoc 2002;133:861-871.

Moore N, Pollack C and Butkerait P. Adverse drug reactions and drug-drug interactions with over-the-counter NSAIDs. Ther Clin Risk Manag 2015;11:1061-1075.

Moore N, Scheiman JM. Gastrointestinal safety and tolerability of oral non-aspirin over-the-counter analgesics. Postgrad Med. 2018;130:188-199.

Moore RA, Wiffen PJ, Derry S, et al. Non-prescription (OTC) oral analgesics for acute pain—an overview of Cochrane reviews. Cochrane Database Syst Rev 2015:CD010794.

Packman B, Packman E, Doyle G, et al. Solubilized ibuprofen: evaluation of onset, relief, and safety of a novel formulation in the treatment of episodic tension-type headache. Headache 2000;40:561-567.

Paul IM, Sturgis SA, Yang C, Engle L, Watts H, Berlin CM, Jr. Efficacy of standard doses of ibuprofen alone, alternating, and combined with acetaminophen for the treatment of febrile children. Clin Ther. 2010;32:2433-2440. doi: 10.1016/j.clinthera.2011.01.006.

Peto R. Experimental survival curves for interval-censored data. J R Stat Soc Ser C Appl Stat. 1973;22:86-91.

Pierce CA, Voss B. Efficacy and safety of ibuprofen and acetaminophen in children and adults: a meta-analysis and qualitative review. Ann Pharmacother. 2010;44:489-506. doi: 10.1345/aph.1M332.

Purssell E. Systematic review of studies comparing combined treatment with paracetamol and ibuprofen, with either drug alone. Arch Dis Child. 2011;96:1175-1179. doi: 10.1136/archdischild-2011-300424.

Rainsford KD. Ibuprofen: pharmacology, efficacy and safety. Inflammopharmacology 2009;17:275-342.

Starkweather A. PM. Enhanced recovery programs and pain management. Top Pain Manag 2017;32:1-12.

Suffredini AF, Noveck RJ. Human endotoxin administration as an experimental model in drug development. Clin Pharmacol Ther. 2014;96:418-422. doi: 10.1038/clpt.2014.146.

Tanner T, Aspley S, Munn A, et al. The pharmacokinetic profile of a novel fixed-dose combination tablet of ibuprofen and paracetamol. BMC Clin Pharmacol 2010;10:10.

Tjolsen A, Lund A and Hole K. Antinociceptive effect of paracetamol in rats is partly dependent on spinal serotonergic systems. Eur J Pharmacol 1991;193:193-201.

Turnbull BW. The empirical distribution function with arbitrarily grouped, censored and truncated data. J R Stat Soc Series B Stat Methodol. 1976;38:290-295.

Wright CE, 3rd, Antal EJ, Gillespie WR, et al. Ibuprofen and acetaminophen kinetics when taken concurrently. Clin Pharmacol Ther 1983;34:707-710.

https://www.clinicaltrials.gov/ct2/show/NCT02761980?term=ibuprofen+acetaminophen&cond=fever&draw=4&rank=1.

Burnett, D., "Correlating drug-binder adhesive strengths measure using Inverse Gas Chromatography with tablet performance", Surface Measurement Systems Ltd., 2014, pp. 1-4.

* cited by examiner

IBUPROFEN AND ACETAMINOPHEN TABLET

BACKGROUND

Ibuprofen (IBU) and acetaminophen (APAP) are among the most widely used analgesic/antipyretic drugs both in the United States and globally. Their efficacy and safety as nonprescription treatments for minor pain and fever in adults and children are well established (see, e.g., Dickman A., "Choosing over-the-counter analgesics," Pharm J. 2008; 281:631; Perrott D A, et al., "Efficacy and safety of acetaminophen vs ibuprofen for treating children's pain or fever: a meta-analysis," Arch Pediatr Adolesc Med. 2004; 158: 521-526; Goldman R D et al., "Antipyretic efficacy and safety of ibuprofen and acetaminophen in children," Ann Pharmacother. 2004; 38:146-150; and Pierce C A and Voss B., "Efficacy and safety of ibuprofen and acetaminophen in children and adults: a meta-analysis and qualitative review," Ann Pharacother. 2010; 44:489-506).

Ibuprofen, a propionic acid derivative nonsteroidal anti-inflammatory drug (NSAID), has been used in the treatment of pain, injury, and illness for its analgesic, anti-inflammatory, and antipyretic effects. It is taken for arthritis, sports injuries, soft tissue trauma, dysmenorrhea, migraine headaches, tension headaches, and dental pain, for example. Ibuprofen is one of the most extensively studied and widely used drugs. It has been estimated that ibuprofen has been used to treat over 100 million patients in at least 100 countries throughout the world. Acetaminophen, N-(4-hydroxyphenyl)acetamide or herein referred to as APAP, was first used in medicine by Van Mering in 1893, but only since 1949 has it gained in popularity as an effective alternative to aspirin for analgesic uses in the over the counter market.

However, for many patients who take over-the-counter (OTC) analgesics, complete relief from pain or fever may be difficult to achieve with a single analgesic or anti-pyretic agent. Unfortunately, further single-dose increases above 400 mg for IBU and 1000 mg for APAP (i.e., the maximum recommended single-dose OTC strength) provide little if any additional therapeutic benefits but may result in a higher risk of adverse events (AEs).

The concept of multimodal analgesia, a process by which different procedures, techniques and/or medications with differing mechanisms of action are used to achieve adequate pain control, was initially brought forth in the 1990s to improve recovery after surgery. Over time, this strategy has become more commonplace and has been associated with improved patient satisfaction and reduced length of hospital stay.

It stands to reason that operationalizing this same concept in the OTC analgesic environment might lead to better pain control compared with that achieved with a single OTC analgesic, and similarly for anti-pyresis.

IBU and APAP are 2 such agents that act via different mechanisms. IBU is a nonsteroidal anti-inflammatory drug (NSAID) that inhibits cyclooxygenase (COX)-1 and COX-2 isoenzymes, blocking the subsequent synthesis of pro-inflammatory prostanoids both in the periphery and in the central nervous system; APAP is believed to act through inhibition of a sub-class of COX enzyme isoforms in the central nervous system (Tanner T et al., "The pharmacokinetic profile of a novel fixed-dose combination tablet of ibuprofen and paracetamol," BMC Clin Pharmacol. 2010; 10:10). Other proposed mechanisms of action for APAP include activation of central serotonergic pain-inhibitory pathways descending from the brain and inhibition of the L-arginine nitric oxide pathway mediated by substance P or N-methyl-D-aspartate (NMDA). In addition, effects on cannabinoid receptors via acetaminophen metabolites have also been proposed (Anderson B J, "Paracetamol (acetaminophen): mechanisms of action," Paediatr Anaesth. 2008; 18:915-921). There have been investigations whether certain combinations may have superior efficacy to either agent alone (Mehlisch D R, "The efficacy of combination analgesic therapy in relieving dental pain," J Am Dent Assoc. 2002; 133:861-871; Beaver W T, "Combination analgesics," Am J Med 1984; 77:38-53).

IBU and APAP do not share metabolic pathways, which diminishes the likelihood of drug-drug interactions (Tanner T et al., "The pharmacokinetic profile of a novel fixed-dose combination tablet of ibuprofen and paracetamol," BMC Clin Pharmacol. 2010; 10:10; Wright C E et al., "Ibuprofen and acetaminophen kinetics when taken concurrently," Clin Pharmacol Ther. 1983; 34:707-710)). Previous pharmacokinetic studies have demonstrated a lack of drug-drug interactions between IBU and APAP. IBU and APAP also have different side-effect profiles. At higher doses and longer durations of treatment, IBU and other NSAIDs are associated with the potential for gastrointestinal, cardiovascular, and renal side effects, while APAP overdose is associated with hepatotoxicity. Therefore, a combination product containing IBU and APAP allows for the use of lower doses of both agents, reducing safety concerns associated with higher doses of either drug such as gastrointestinal bleeding or hepatotoxicity (Moore N and Scheiman J M, "Gastrointestinal safety and tolerability of oral non-aspirin over-the-counter analgesics," Postgrad Med. 2018; 130: 188-199) while at the same time satisfying the unmet need for a more convenient non-prescription analgesic/antipyretic with a favorable safety profile.

Previous studies on a fixed-dose combination (FDC) of IBU 200 mg with APAP 500 mg in postsurgical dental pain found that the FDC provided significantly better analgesia versus APAP 1000 mg alone and numerically better analgesia than IBU 400 mg alone, without emergent safety concerns (see Mehlisch D R et al., "Comparison of the analgesic efficacy of concurrent ibuprofen and paracetamol with ibuprofen or paracetamol alone in the management of moderate to severe acute postoperative dental pain in adolescents and adults: a randomized, double-blind, placebo-controlled, parallel-group, single-dose, two-center, modified factorial study," Clin Ther. 2010; 32:882-895; Mehlisch D R et al., "A single-tablet fixed-dose combination of racemic ibuprofen/paracetamol in the management of moderate to severe postoperative dental pain in adult and adolescent patients: a multicenter, two-stage, randomized, double-blind, parallel-group, placebo-controlled, factorial study," Clin Ther. 2010; 32:1033-1049; and Doherty M et al., A randomised controlled trial of ibuprofen, paracetamol or a combination tablet of ibuprofen/paracetamol in community-derived people with knee pain," Ann Rheum Dis. 2011; 70:1534-1541).

Furthermore, certain combinations of IBU and APAP have been investigated for fever reduction (Malya R R, "Does combination treatment with ibuprofen and acetaminophen improve fever control?," Ann Emerg Med. 2013; 61:569-570; Paul I M et al., "Efficacy of standard doses of ibuprofen alone, alternating, and combined with acetaminophen for the treatment of febrile children," Clin Ther. 2010; 32:2433-2440; Purssell E., "Systematic review of studies comparing combined treatment with paracetamol and ibuprofen, with either drug alone," Arch Dis Child. 2011; 96:1175-1179).

WO2007/034135 (Reckitt Benckiser Healthcare (UK) Ltd) discloses a fixed dose combination product comprising 200 mg ibuprofen and 500 mg paracetamol (acetaminophen). Such a product is marketed by Reckitt Benckiser as Nuromol® for the temporary relief of mild to moderate pain associated with migraine, headache, backache, period pain, dental pain, rheumatic and muscular pain, pain of non-serious arthritis, cold and flu symptoms, sore throat and fever. The administration regimen is one or two tablets to be taken up to three times per day, leaving at least six hours between doses, up to a maximum of six tablets (3000 mg paracetamol, 1200 mg ibuprofen) in any 24 hour period. The tablet is indicated to comprise croscarmellose sodium, microcrystalline cellulose, colloidal anhydrous silica, magnesium stearate, and stearic acid, with a film coating comprising polyvinyl alcohol, titanium dioxide, talc, macrogol, potassium aluminum silicate (E555), and polysorbate.

U.S. Pat. No. 10,532,036 (Atkinson) discloses a fixed dose combination pharmaceutical product for the treatment of pain including about 125 mg to about 150 mg ibuprofen and about 475 mg to about 500 mg paracetamol. The ratio of paracetamol:ibuprofen in a single therapeutic dose is about 50:15.

U.S. Published Application 2019/0350883 (Chau) describes solid dosage forms such as a single tablet that contains about 1000 mg of acetaminophen and 400 mg of ibuprofen or a single tablet that contains about 650 mg of acetaminophen and about 400 mg of ibuprofen.

Further, certain processing steps are utilized to accurately formulate and/or manufacture solid dose products. "Wet Granulation" methods can be used where the flow properties of a compound such as an active pharmaceutical ingredient ("API") are poor which result in content uniformity issues when formulated as a dry blend. Wet granulation is commonly used to improve the processing characteristics of a powder blend, including improved flowability, contentuniformity and more uniform particle size. Wet granulation is used to improve flow, compressibility, bio-availability, homogeneity, electrostatic properties, and stability of solid dosage forms. Granulation is often required to improve the flow of powder mixtures and mechanical properties of tablets. Granules are usually obtained by adding liquids (binder or solvent solutions). Larger quantities of granulating liquid produce a narrower particle size range and coarser and harder granules, i.e. the proportion of fine granulate particles decreases. The particle size of the granulate is determined by the quantity and feeding rate of granulating liquid.

Wet granulation methods can be used where the flow properties of a compound such as an active pharmaceutical ingredient ("API") are poor which result in content uniformity issues when formulated as a dry blend. Wet granulation is commonly used to improve the processing characteristics of a powder blend, including improved flowability, content uniformity and more uniform particle size. The use of water and heat in wet granulation may cause chemical degradation or physical form conversion.

The variables faced in the processing of the granules can lead to significant tableting problems. Properties of granules formed can be affected by viscosity of granulating solution, rate of addition of granulating solution, type of mixer used and duration of mixing method and rate of dry and wet blending. The above variables can change the density and the particle size of the resulting granules and may have a major influence on fill weight and compaction qualities.

SUMMARY OF THE INVENTION

The present invention provides novel compositions, tablet formulations, methods of treatment and methods of manufacture of large scale, commercially viable ibuprofen and acetaminophen tablets. The unique characteristics and synergistic effects resulting from the disclosed formulations, methods of treatment and methods of manufacture demonstrate a product with optimal analgesia, safety profiles and large-scale manufacturability. The inventions described herein surprisingly show the unique formulation and method of manufacturing for a large-scale commercial batch of a novel ibuprofen and acetaminophen tablet. In particular, contrary to teachings in the art, the use of the disclosed multi-step mixing, water in the wet granulation steps and heating process did not cause the expected chemical degradation or physical form conversion.

In a further aspect the invention provides an oral pharmaceutical composition suitable for compression tableting comprising the active ingredients ibuprofen, in an amount of 100 mg to 300 mg and acetaminophen, in an amount of 150 mg to 600 mg, wherein the ratio of ibuprofen to acetaminophen is 1:3 to 1:1 by weight; wherein the composition comprises intragranular and extragranular components, wherein the intragranular components comprise the active ingredients; a binding agent selected from the group consisting of pregelatinized starch, celluloses such as microcrystalline cellulose and hypromellose, gelatin, sugars, polyethylene glycol, waxes, natural and synthetic gums, synthetic polymers, and mixtures thereof; a disintegrating agent; and a glidant; and wherein the extragranular components comprise a disintegrating agent, a glidant and a lubricant.

In another aspect, the invention provides an oral pharmaceutical composition suitable for tableting, comprising the active ingredients ibuprofen and acetaminophen, wherein the ibuprofen is present in an amount of 100 to 300 mg and acetaminophen is present in an amount of 150 to 600 mg, wherein the ratio of ibuprofen to acetaminophen is 1:3 to 1:1 (e.g., 1:2) by weight; and, wherein the composition further comprises intragranular and extragranular components, wherein the intragranular components comprise the active ingredients, a binding agent, a disintegrating agent, and a glidant; and the extragranular components comprise a disintegrating agent, a glidant and a lubricant, and wherein the composition is essentially free of unmodified starch.

By "essentially free" is meant about 1% or less, and preferably about 0.5% or less, and most preferably 0%, based on the composition.

In a further aspect, the invention comprises a method for treating a mammalian subject in need thereof to relieve pain and/or inflammation, comprising orally administering to the subject a pharmaceutical composition comprising the active ingredients, ibuprofen in an amount of 250 mg and acetaminophen in an amount of 500 mg; and said composition further comprising: intragranular and extragranular components, the intragranular components comprising the active ingredients, a binding agent, a disintegrating agent and a glidant, and the extragranular components comprising a disintegrating agent, a glidant and a lubricant, the composition being essentially free of unmodified starch; and said composition being administered in a single or divided doses;

said administration being optionally repeated at intervals of 8 hours until the subject attains relief from pain and/or inflammation.

In a preferred aspect, the invention comprises the method wherein the composition is administered in divided doses, and wherein the divided doses consist of two tablets each comprising 125 mg ibuprofen and 250 mg acetaminophen.

The method of the invention contemplates a total daily ibuprofen dose of 750 mg and a total daily acetaminophen dose of 1500 mg, both of which are considerably lower than the currently approved OTC maximum daily doses for the agents (1200 and 4000 mg, respectively).

In a further aspect, the invention comprises a method for reducing fever in a mammalian subject in need thereof, comprising administering to the subject an oral pharmaceutical composition comprising the active ingredients, ibuprofen in an amount of 250 mg and acetaminophen in an amount of 500 mg, in a single or divided doses, said administration being optionally repeated until the subject attains fever reduction.

In a further aspect, the composition comprises intragranular and extragranular components, wherein the intragranular components comprise the active ingredients, a binding agent, a disintegrating agent and a glidant, and the extragranular components comprise a disintegrating agent, a glidant and a lubricant, the composition being essentially free of unmodified starch.

In one aspect, the fever-reducing composition is orally administered in divided doses each comprising 125 mg ibuprofen and 250 mg acetaminophen.

In a still further aspect, the invention comprises the method wherein the composition is administered in divided doses, and wherein the divided doses consist of two tablets each comprising 125 mg ibuprofen and 250 mg acetaminophen.

The invention also contemplates processes for making tablets of the invention.

BRIEF DESCRIPTION OF THE DRAWINGS

Embodiments will be described with reference to the following figures, in which like numerals represent like items throughout the figures, and in which.

DETAILED DESCRIPTION OF THE INVENTION

Figure 1A:
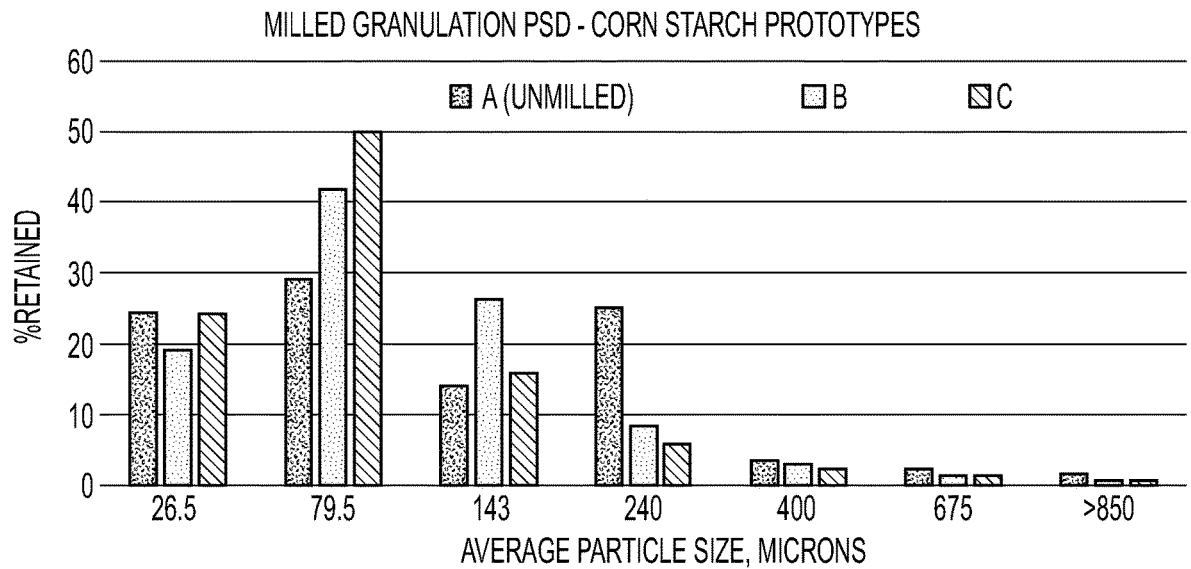
FIGS. 1A and 1B are bar charts depict the particle size distribution (PSD) of milled granulations prepared from prototypes A-C and D-F, respectively, with the exception that A was unmilled (Example 2).

Applicants have surprisingly discovered a composition of ibuprofen and APAP that synergistically provides for both an effective pain treatment, a minimization of adverse events, a minimization of degradants and contaminants, and a minimization of manufacturing related issues particularly in commercial large-scale batch manufacture.

Further a composition as described herein comprising ibuprofen in a dosage amount of 250 mg and acetaminophen in a dosage amount of 500 mg, suitably delivered in divided doses (e.g., as two tablets each comprising 125 mg ibuprofen and 250 mg acetaminophen) has been found to provide an effective antipyretic treatment offering faster onset of antipyresis that lasts longer than the same doses of ibuprofen and acetaminophen alone. In particular, the composition has been demonstrated to provide a statistically significant reduction of fever in the period from 0 to 2 hours after administration, relative to placebo, while ibuprofen and acetaminophen alone did not. Additionally, co-administration of ibuprofen 250 mg and acetaminophen 500 mg was found to reduce fever significantly better than placebo over 0-8 hours; and the combination was numerically better over this period than the individual actives.

Tablets of the invention may be uncoated or coated. Coated tablets may be polished or unpolished. The most preferable form of tablet for the inventions disclosed is film coated and polished.

One aspect of the invention is a granulate i.e. material that has been adapted and preprocessed by suitable means such as aqueous or non-aqueous granulation to form granules. For purposes herein a component of the granulate is referred to as 'intragranular' or an 'intragranular component' whereas a component that is external to, and preferably in admixture with, the granulate is referred to as 'extragranular' or an 'extragranular component'. The granulate comprises acetaminophen, ibuprofen, a binding agent, a disintegrating agent and a glidant. The intragranular components may comprise one or more additional ingredients including but not limited to a processing aid, diluent or filler, colorant, dye, sweetening agent or a mixture thereof. The granulate may optionally be combined (and preferably mixed or blended) with one or more suitable extragranular components to form a pharmaceutical composition.

A composition of the invention is preferably in the form of a swallow tablet, i.e. a tablet that is intended to be swallowed whole, without being chewed or otherwise dispersed in the mouth, nor dissolved or suspended in water, prior to administration.

The term "tablet" as used herein includes tablets of any shape, and includes caplets, which are tablets having a capsule shape. Suitably a tablet according to the invention has a hardness between 80-200 N, a disintegration time of about 30 to about 240 seconds, and friability values below about 1.0% after 500 revolutions.

A tablet according to the invention comprises ibuprofen. Ibuprofen, as referred to herein, is 2-(4-isobutylphenyl) propionic acid, or a pharmaceutically acceptable salt thereof, such as the sodium, arginine, lysine, or histidine salt of ibuprofen. The most preferable form of ibuprofen for the inventions disclosed is the free acid form. Suitably the ibuprofen is present in a tablet according to the invention in an amount ranging from 15% to 30% by weight of the tablet, such as 20% to 28% by weight of the tablet. In some embodiments a tablet of the invention comprises ibuprofen in an amount from 100 mg to 150 mg e.g. 110 mg to 140 mg, such as about 125 mg, per tablet. In an alternate embodiment, the ibuprofen may be present in an amount of, e.g., 250 mg.

A tablet according to the invention comprises acetaminophen. Acetaminophen, as referred to herein, includes any pharmaceutically acceptable isomer, ester, polymorph or salts thereof. Suitably the acetaminophen is present in a tablet according to the invention in an amount ranging from 40% to 60% by weight of the tablet, such as 45% to 55% by weight of the tablet. In one embodiment the acetaminophen is present in an amount from 200 mg to 300 mg e.g. 230 mg to 270 mg, such as about 250 mg. In an alternate embodiment, the acetaminophen may be present in an amount of, e.g., 500 mg.

Suitably the ratio of ibuprofen to acetaminophen is in the range of 1:3 to 1:1.5, for example about 1:2.

All amounts recited herein are with reference to ibuprofen free acid or acetaminophen. Pharmaceutically acceptable salts, or esters, or other derivatives may be employed in dose adjusted amounts equivalent to the doses recited herein for free ibuprofen or acetaminophen, as the case may be.

Also contemplated are the inclusion of one or more non-pharmaceutically active excipients in the compositions of the present invention. These include, but are not limited to, controlled release agents, diluents, binders, disintegrants, surface active agents, glidants, lubricants, colorants, coating substances, surfactants and many other raw materials that impart different properties to the final solid dosage product.

A tablet according to the invention comprises a binding agent. A binding agent or binder is an agent that imparts cohesive qualities to a powdered material. Binding agents impart cohesiveness to a tablet formulation which insures the tablet remains intact after compression, as well as improving the free-flowing qualities by the formulation of granules of desired hardness and size. Suitable binding agents of use in the present invention are selected from the list consisting of pregelatinized starch, celluloses such as microcrystalline cellulose and hypromellose, gelatin, sugars (including sucrose, glucose, dextrose, lactose and sorbitol), polyethylene glycol, waxes, natural and synthetic gums, e.g., acacia, tragacanth, sodium alginate, and synthetic polymers such as polymethacrylates and polyvinylpyrrolidone, and mixtures thereof.

Unexpectedly, despite its widespread usage as a tablet binder, an unmodified starch such as corn (maize) starch gave excessively fine granules having poor compressibility, and as such proved unsuitable for use as a binder in the present compositions. By comparison, it has now been found, and is an aspect of this invention, that the selection of a binding agent comprising, or consisting essentially of, pregelatinized starch (optionally with a cellulose such as Hypromellose), provides ibuprofen and acetaminophen-containing granules having favorable properties including granulation performance, compression blend performance and tablet strength that were not attainable using an unmodified starch.

As will be understood by the worker in the art, the term, "unmodified starch" (alternately referred to in the art as "common" or "regular" or "native" starch) refers to the carbohydrate (generally made up of linear amylose and branched amylopectin) that is derived from the corn (maize) kernel or other natural sources, such potato or rice, generally by a process of wet milling and drying, without chemical modification (see "Corn Starch", published by Corn Refiners Association, 11$^{th}$ Ed., 2006). Such unmodified starch, being insoluble in cold water, is typically prepared in the form of a paste using hot water.

By comparison, pregelatinized starch, while being derived from natural sources such as corn (maize) starch, potato or rice, is starch that has been chemically and/or mechanically processed to rupture all or part of the granules in the presence of water, i.e. so that the product is gelatinized, and subsequently dried. An example of a suitable pregelatinized product is that produced from Dent Corn (regular corn) having a range of amylose of about 22-28% and amyloptectin making up the remainder. Some types of pregelatinized starch may be further modified to render them compressible and flowable in character (U.S. Pharmacopeia 37-NF32).

Fully pregelatinized starch is characterized in being soluble in cold water, eliminating the need to prepare heated starch pastes for wet granulation applications; by eliminating the pre-solubilization step, the starch can be added directly to granulation equipment with other actives and excipients, and water can then be used as the granulation fluid.

Partially pregelatinized starch (PPS) contains soluble (gelatinized) and in soluble fractions. In most cases, the insoluble fraction comprises intact starch grains. (see *Pharmaceutical Excipients—Properties Functionality, and Applications in Research and industry*, edited by OMY Koo, John Wiley & Sons, 2016; C. Cunningham, C, "Starch Contrasts," Colorcon)

A suitable example of a pregelatinized starch useful herein has cold water solubility (i.e. at about 25° C.) of at least 50%, preferably at least 75%, and more preferably about 90% or greater.

Commercially available fully or partially pregelatinized starch excipients include Unipure WG 220 (Ingredion); National Starch 1551; Ingredion WG220; Colorcon Starch 1500; Roquette Lycatab PGS; and Seppic PC-10 Starch.

It is preferred to use a fully pregelatinized starch such as Unipure WG 220 (Ingredion) in the compositions of the invention.

The compositions of the invention are "essentially free of unmodified starch" in that unmodified starch (e.g., corn or maize starch) is not provided as an excipient to the composition in the course of its preparation. The compositions of the invention will therefore preferably be devoid of, or have no more than 1%, of unmodified starch other than any amounts of unmodified starch persisting as an intrinsic component of the fully or partially pregelatinized starch excipient.

In one embodiment of the invention, the binding agent comprises, or consists essentially of, pregelatinized starch, optionally together with a cellulose such as Hypromellose.

In one embodiment, pregelatinized starch (optionally with Hypromellose) is the sole binding agent.

Generally, the binding agent is present in an amount from about 1% to about 25% by weight of the tablet. While a binding agent is present as an intragranular component, it is recognized that a modest amount of binding agent e.g. up to about an additional 5% to 10%, by weight of the intragranular binding agent, may also be present extragranularly. Typically, when present in a tablet of the invention, pregelatinized starch is present intragranularly in an amount from about 4% to 25%, typically from about 5% to 20% for example from about 8% to 15% by weight of the tablet.

Hypromellose (also referred to in the art as hydroxypropyl methyl cellulose or HPMC) is a methyl and hydroxypropyl mixed ether of cellulose. Suitably, Hypromellose of use in the invention comprises, on a dried basis, methoxy and hydroxypropoxy groups conforming to the limits set forth below:

| | Methoxy (%) | | Hydroxypropoxy (%) | |
|---|---|---|---|---|
| Substitution type | Min | Max | Min | Max |
| 2910 | 28.0 | 30.0 | 7.0 | 12.0 |

Further a Hypromellose of use herein comprises a low nominal viscosity, suitably in the range 2-70 mPa·s, such as 3 to 25 mPa·s e.g. 10-20 mPa·s, as determined by a standard viscosity method used in the art e.g. measured at 20° C. with a 2% solution e.g. using a Ubbelhode viscometer. Suitably, the Hypromellose comprises a weight average molecular weight in the range 20,000 to 100,000, for example 30,000 to 70,000 such as about 52,000.

Examples of suitable commercially available grades of Hypromellose are those known as Hypromellose "E" types, such as E3, E5, E15, E50, available from Ashland Inc, Covington, KY USA, and have the following properties:

| Grade | Weight Average Molecular Weight | Solution Concentration | Nominal Viscosity (mPa · s) |
|---|---|---|---|
| E3 Pharm | 20,000 | 2% | 2.4-3.6 |
| E5 Pharm | 34,500 | 2% | 4.0-6.0 |
| E6 Pharm | 40,000 | 2% | 4.8-7.2 |
| E15 PH PRM | 52,000 | 2% | 12-18 |
| E50 PH PRM | 91,000 | 2% | 40-60 |

Typically, when present in a tablet of the invention, Hypromellose is present intragranularly in an amount not more than 2.5% by weight of the tablet, for example from about 1% to about 2% by weight of the tablet.

In one embodiment a tablet of the invention comprises a first binding agent and a second binding agent. Suitably pregelatinized starch is a first binding agent and Hypromellose is a second binding agent. Advantageously, incorporation of a small amount of Hypromellose (relative to pregelatinized starch) as a second binding agent has a positive impact, albeit a modest one, on tablet hardness. Suitably the weight ratio of pregelatinized starch:Hypromellose is about is about 7:1 to about 12:1, e.g., 7:1 to 11:1, for example about 10:1. In one embodiment pregelatinized starch is present as a first binding agent in an amount ranging from about 8% to about 15% by weight of the tablet and Hypromellose is present as a second binding agent in an amount ranging from about 1% to about 2% by weight of the tablet.

It will be recognized that while being used as a binder, the pregelatinized starch may also be serving as a disintegrant in the compositions of the invention.

A tablet according to the invention comprises a component that functions as a disintegrant, such as one or more disintegrating agents. A disintegrant or disintegrating agent is a substance, or a mixture or combination of substances, added to a tablet formulation to facilitate tablet breakup or disintegration after administration. Materials serving as disintegrants have been classified chemically as starches, clay, celluloses, aligns, gums and cross-linked polymers. Suitable disintegrating agents include a non-super disintegrant, a super disintegrant or a combination of both. Suitable non-super disintegrants of use in the invention are selected from pregelatinized starch, microcrystalline cellulose or powdered cellulose. In one embodiment the non-superdisintegrant is pregelatinized starch. It is recognized in the art that some excipients may perform more than one role in a given pharmaceutical formulation. For example certain excipients such as pregelatinized starch and microcrystalline cellulose (hereinbefore identified as binding agents) function as both binders and disintegrants Accordingly it will be understood that the same excipient may act as both binding agent and disintegrating agent. In such cases inclusion of a disintegrating agent in addition to a binding agent is entirely optional. Equally, in such cases, inclusion of a binding agent in addition to a disintegrating agent is entirely optional.

Suitably a non-super disintegrant is present intragranularly or extragranularly or both in an amount ranging from about 4% to about 25%, for example 5% to 20% such as 8% to 15% by weight of the tablet.

"Super disintegrants" represent a class of disintegrating agent which may generally be used in lower amounts in pharmaceutical preparations, as compared to conventional disintegrants. Examples of super disintegrants include modified celluloses such as croscarmellose, the sodium salt of carboxymethyl cellulose; sodium starch glycolate and cross-linked polyvinyl pyrrolidone. In one embodiment the disintegrating agent comprises a super disintegrant which is croscarmellose. A super disintegrant may be present intragranularly, extragranularly or both intragranularly and extragranularly. In one embodiment the super disintegrant is present both intragranularly and extragranularly. Suitably a super disintegrant will be present intragranularly, extragranularly or both intragranularly and extragranularly in an amount from about 0.5% to about 5% by weight, for example from about 1.5% to about 3.5% by weight of the tablet. Suitably the combined amount of super disintegrant present intragranularly and extragranularly will be from about 1% by weight to about 10%, for example from about 3% to about 7% by weight of the tablet.

A tablet according to the invention comprises a glidant. Glidants are substances which improve the flow characteristics of a powder mixture. Examples of glidants include, but are not limited to, silicon dioxide (e.g., colloidal silicon dioxide), talc or mixtures thereof. The most preferred glidant for the inventions disclosed is colloidal silicon dioxide. Suitably the glidant is present intragranularly, extragranularly or both intragranularly and extragranularly. Generally, the glidant is present in an amount of from about 0.1% to about 10% of the weight of the tablet and more specifically from about 1% to about 5% of the weight of the tablet. The most preferred amount of glidant for the inventions disclosed is from about 2% to about 3% of the weight of the tablet. For example, a glidant will be present intragranularly, extragranularly, or both intragranularly and extragranularly in an amount from about 0.5% to about 2% by weight of the tablet, for example from about 1% by weight of the tablet. For example, the combined amount of glidant present intragranularly and extragranularly will be in an amount from about 1% to about 4% by weight, for example about 2% by weight of the tablet.

A tablet according to the invention comprises a lubricant. Lubricants have a number of functions in tablet manufacture. They prevent adhesion of the tablet material to the surface of the dies and punches, reduce interparticle friction, facilitate the ejection of the tablets from the die cavity and may improve the rate of flow of the tablet granulation. Examples of suitable lubricants include, magnesium stearate, calcium stearate, stearic acid, glyceryl dibehenate, talc, sodium lauryl sulfate, sodium stearyl fumarate, polyethylene glycol or mixtures thereof. Glyceryl dibehenate comprises a mixture of various esters of behenic acid and glycerol, including glyceryl (mono) behenate. In one embodiment the lubricant comprises glyceryl dibehenate.

A common problem that can arise with tableting of certain actives, such as ibuprofen, is that of "picking and sticking". Sticking occurs when granules attach themselves to the faces of tablet press punches. Picking is a more specific term that describes product sticking only within the letters, logos or designs on the punch faces. Advantageously use of monoesters, diesters or triesters of glycerin with saturated aliphatic carboxylic acids having from 18 to 24 carbon atoms, such as 22 carbon atoms, yields the formation of good tablets which have little to no sticking and picking. and which have low ejection forces from the press Generally, the lubricant is present in an amount from about 0.25% to about 3%, e.g., from about 0.5% to about 2%, by weight of the tablet. The most preferred amount of lubricant for the inventions disclosed is from about 1% to about 1.5% of the weight of the tablet. A lubricant will generally be present extragranularly.

Preferably the milled granulate of the invention will comprise a population of granules having a d50 (for example as described in Example 2) of 100 or greater, for example, a d50 of about 100-200, or about 110-180, e.g., about 150.

As used herein, the term "about" (or "approximately") means that a particular value can have a range acceptable to those of skill in the art given the nature of the value and method by which it is determined. Preferably, when considering the term "about" in the context of an amount of an ingredient, "about" means plus or minus 5% of the ingredient. Most preferably, when considering the term "about" in the context of an amount of an ingredient, "about" means plus or minus 2% of the amount of ingredient.

If desired, other ingredients, such as diluents, stabilizers and anti-adherents, conventionally used for pharmaceutical formulations may be included in the present formulations. Optional ingredients include coloring and flavoring agents which are well known in the art.

In its various embodiments, the invention comprises:
A composition suitable for tableting comprising:
(i) the active ingredients ibuprofen and acetaminophen, present intragranularly;
(ii) 5% to 20% by weight pregelatinized starch, present intragranularly;
(iii) 0.5% to 2.5% by weight Hypromellose, present intragranularly;
(iv) 0.5% to 3% by weight of glyceryl dibehenate, present extragranularly;
(v) 1% to 10% by weight croscarmellose, present intragranularly and extragranularly;
(vi) 1% to 5% by weight silicon dioxide, present intragranularly and extragranularly;
and wherein the composition is essentially free of unmodified starch.

A composition suitable for tableting comprising:
(i) the active ingredients ibuprofen and acetaminophen, present intragranularly;
(ii) 8% to 15% by weight pregelatinized starch, present intragranularly;
(iii) 1% to 2% by weight Hypromellose, present intragranularly;
(iv) 1% to 2% by weight of glyceryl dibehenate, present extragranularly;
(v) 5% to 8% by weight croscarmellose, present intragranularly and extragranularly;
(vi) 2% to 4% by weight silicon dioxide, present intragranularly and extragranularly;
and wherein the composition is essentially free of unmodified starch.
(all weight percentages being based on the total composition)

In a preferred aspect, the compositions of the invention comprise ibuprofen in an amount of 100 mg to 200 mg (e.g., 110 mg to 140 mg; e.g., 125 mg) and acetaminophen in an amount of 200 mg to 300 mg (e.g., 230 mg to 270 mg; e.g., 250 mg); or alternatively, ibuprofen may be present in an amount of 200 mg to 300 mg (e.g., 230 mg to 270 mg; e.g., 250 mg) and the acetaminophen in an amount of 400 mg to 600 mg (e.g., 500 mg), wherein in each case the ratio of ibuprofen to acetaminophen is about 1:3 to 1:1.5 (e.g., 1:2) by weight.

Thus a particular embodiment of a composition comprises:
125 mg ibuprofen
250 mg acetaminophen,
5% to 20% by weight pregelatinized starch;
0.5% to 2.5% by weight Hypromellose;
0.5% to 3% by weight of glyceryl dibehenate
1% to 10% by weight croscarmellose; and
1% to 5% by weight colloidal silicon dioxide;
wherein the composition is essentially free of unmodified starch.

Another embodiment of a composition of the invention comprises:
125 mg ibuprofen;
250 mg acetaminophen;
8% to 15% by weight pregelatinized starch;
1% to 2% by weight Hypromellose;
1% to 2% by weight of glyceryl dibehenate;
5% to 8% by weight croscarmellose; and
2% to 4% by weight colloidal silicon dioxide.
wherein the composition is essentially free of unmodified starch
(all weight percentages being based on the total composition).

The invention further includes a compressed tablet for oral administration comprising:
125 mg ibuprofen;
250 mg acetaminophen;
about 12% by weight pregelatinized starch;
about 2% by weight Hypromellose;
about 1% by weight of glyceryl dibehenate;
about 7% by weight croscarmellose; and
about 3% by weight colloidal silicon dioxide,
all weight percentages being based on the uncoated tablet core.

An example of such a tablet consists of the following excipients in the uncoated tablet core:
Ibuprofen, 125 mg;
Acetaminophen, 250 mg;
Hypromellose, about 8 mg;

Croscarmellose Sodium, about 33 mg;
Colloidal Silicon Dioxide, about 14 mg;
Pregelatinized Starch, about 60 mg; and
Glyceryl dibehenate, about 7 mg.

As used herein, large scale batch manufacturing refers to making batches of commercially viable tablets in quantities larger than 300,000 tablets in a single batch or sub-batch. Preferably, batches or sub-batches range from 300,000 tablets to 4,000,000 tablets. Most preferably, batches are made up from one or more sub-batches. Most preferably, sub-batches ranging from 500,000 to 750,000 tablets.

Another aspect of the invention provides a process for the preparation of a tablet. The process comprises preparing a granulate as described above and admixing the granulate with any desired extragranular component to form a master blend and compressing the master blend into tablets.

In another aspect, the invention a process for manufacturing a tablet according to the invention comprising the steps of:
  (a) forming a Granulating Solution by adding a binding agent to water in a mixing tank and mixing;
  (b) forming a Pre-Blend by adding the glidant and the intraganular disintegrating agent in a blending tank and blending;
  (c) forming a Wet Granulate by combining the Granulating Solution, Pre-Blend, the ibuprofen, the acetaminophen and the intragranular disintegrating agent;
  (d) optionally wet milling said Wet Granulate;
  (e) forming a Tablet Mix by drying said Wet Granulation in a Drier until said Wet Granulation reaches a fluid content below 2.0%;
  (f) pressing said Tablet Mix into a tablet in a tablet press by applying at least 15 kN of force (i.e. hardness of 80N); and
  (g) optionally coating said tablets.

In a further aspect, the invention comprises a method for treating a mammalian subject in need thereof to relieve pain and/or inflammation and/or fever, comprising orally administering to the subject a pharmaceutical composition, said composition comprising the active ingredients, ibuprofen in an amount of 250 mg and acetaminophen in an amount of 500 mg; said composition further comprising: intragranular and extragranular components, the intragranular components comprising the active ingredients, a binding agent, a disintegrating agent and a glidant, and the extragranular components comprising a disintegrating agent, a glidant and a lubricant, the composition being essentially free of unmodified starch; and said composition being administered in single or divided doses;
  said administration being optionally repeated at intervals of 8 hours until the subject attains relief from pain and/or inflammation.

The composition may be administered in divided doses each comprising 125 mg ibuprofen and 250 mg acetaminophen.

The composition may be administered in divided doses each comprising 125 mg ibuprofen and 250 mg acetaminophen, wherein the divided dose consists of two tablets.

An appropriate treatment regimen may consist of the oral administration of the two tablets every 8 hours until the subject achieves relief from pain, resulting in a total daily IBU dose of 750 mg and a total daily APAP dose of 1500 mg, both of which are considerably lower than the currently approved OTC maximum daily doses for the agents (1200 and 4000 mg, respectively.

In general, no more than 6 tablets should be taken over 24 hours.

The compositions of the invention may be administered for the temporary relief of minor aches and pains due to conditions selected from one or more of headache, toothache, backache, menstrual cramps, muscular aches, and minor pain of arthritis.

In one aspect there is provided a composition as defined hereinabove for use in therapy.

In one aspect there is provided a composition as defined hereinabove for use in the treatment of pain and/or inflammation, or for anti-pyresis (fever reduction).

In one aspect there is provided use of a composition as defined hereinabove in the manufacture of a medicament for the treatment of pain and/or inflammation, or for anti-pyresis.

Thus the invention also includes a method for reducing fever in a mammalian subject in need thereof, comprising orally administering to the subject a pharmaceutical composition comprising the active ingredients, ibuprofen in an amount of 250 mg and acetaminophen in an amount of 500 mg, in a single or divided doses, said administration being optionally repeated until the subject attains fever reduction.

The composition may be administered in divided doses each comprising 125 mg ibuprofen and 250 mg acetaminophen.

The composition may further comprise intragranular and extragranular components, the intragranular components comprising the active ingredients, a binding agent, a disintegrating agent and a glidant, and the extragranular components comprising a disintegrating agent, a glidant and a lubricant, the composition being essentially free of unmodified starch.

The composition may be administered in divided doses comprising 125 mg ibuprofen and 250 mg acetaminophen, wherein the divided doses consist of two tablets.

In one aspect there is provided a composition as defined hereinabove for use in the reduction of fever.

In one aspect there is provided use of a composition as defined hereinabove in the manufacture of a medicament for the reduction of fever.

Unless otherwise indicated, all weight percentages recited herein with reference to a component or ingredient of a composition are based on the total composition. Where the composition is a tablet, unless otherwise indicated, all weight percentages recited herein are based on the weight of the tablet exclusive of any film coating (i.e. tablet core).

The following Examples illustrate the invention.

Example 1. Prototype Tablet Formulation

One embodiment of an Ibuprofen 125 mg/Acetaminophen 250 mg tablet is an immediate release yellow, film-coated, capsule-shaped tablet printed on one side in black ink.

TABLE 1

Ibuprofen 125 mg/Acetaminophen 250 mg Tablet.

| Ingredient | Function | Reference to Standard | Unit formula mg/unit | %$^b$ | %$^c$ |
|---|---|---|---|---|---|
| Tablet Core | | | | | |
| Ibuprofen | Active | USP | 125.00 | 24.33 | 25.19 |
| Acetaminophen | Active | USP | 250.00 | 48.66 | 50.38 |
| Hypromellose (E15) | Binder | USP | 7.50 | 1.46 | 1.51 |
| Croscarmellose Sodium | Disintegrating Agent | NF | 33.25 | 6.47 | 6.70 |

TABLE 1-continued

Ibuprofen 125 mg/Acetaminophen 250 mg Tablet.

| Ingredient | Function | Reference to Standard | Unit formula | | |
|---|---|---|---|---|---|
| | | | mg/unit | %[b] | %[c] |
| Colloidal Silicon Dioxide | Glidant | USP | 14.00 | 2.73 | 2.82 |
| Pregelatinized Starch (Corn) | Binder, Disintegrating Agent | NF | 60.00 | 11.68 | 12.09 |
| Purified Water | Processing Aid | USP | —[a] | —[a] | —[a] |
| Glyceryl Dibehenate | Lubricant | NF | 6.50 | 1.27 | 1.31 |
| Film Coat and Polish | | | | | |
| Opadry II, Yellow 49B120000 | Film Coat | In-House | 17.36 | 3.38 | |
| Purified Water | Coating Dispersant | USP | —[a] | —[a] | |
| Carnauba Wax #1 Yellow Powder | Polishing Agent | NF | 0.03 | 0.01 | |
| Printing ink | | | | | |
| Opacode Black NS-78-17821 | Pharmaceutical Ink | In-House | 0.09 | 0.02 | |
| Isopropyl Alcohol | Solvent/Diluent | USP | —[a] | —[a] | |

[a] removed during processing
[b] based on coated tablet
[c] based on uncoated tablet Excipients:

All of the excipients utilized in the Ibuprofen 125 mg/Acetaminophen 250 mg Tablets, with the exception of Opadry II Yellow film coat and Opcode Black ink, are compendial and considered to be "generally recognized as safe" (GRAS). The subcomponents of the film coat and ink are compendial and considered to be safe for use in the US and Canada. The Opacode Black Ink used in this product is included in the FDA Inactive Ingredient Database.

Tablet Core Components:

Croscarmellose sodium is added both intragranularly and extragranularly as a disintegrating agent. Hypromellose was added intragranularly as a binder. Glyceryl dibehenate was added extragranularly as a lubricant. Purified water was added intragranularly as a binder and is essentially removed during processing. Colloidal silicon dioxide was added both intragranularly and extragranularly as a glidant. Pregelatinized starch was added intragranularly as a binder and disintegrating agent.

Based on early formulation studies, the superiority of intragranular pregelatinized starch over corn starch, either alone or in combination with microcrystalline cellulose, has been demonstrated. The addition of hypromellose to the pregelatinized starch prototype (low-level) slightly improved the tablet hardness. Therefore, pregelatinized starch in combination with hypromellose were used as intragranular binders for further formulation development.

Further, the Ibuprofen 150 mg/Acetaminophen 250 mg prototype was successfully compressed. The hardness profile showed tablet hardness between 80-200 (e.g., 98-196) N. Tablet cores compressed between 15 kN and 30 kN (e.g., 20-24 kN) compression force had disintegration times ranging from 41 seconds to 192 seconds and friability values below 1.0% after 500 revolutions.

Film Coating Components:

Opadry II Yellow was used to form a cosmetic film coat over the core. Purified water is the film coating dispersant and was essentially removed during processing. The film coated cores were polished with carnauba wax. Other coats and other film coats are known in the art and contemplated herein.

Printing Components.

Opacode Black ink was used for printing with isopropyl alcohol as a printing solvent. The alcohol was essentially removed during processing. Other inks are known in the art and contemplated herein.

Example 2

In order to evaluate corn starch vs. pregelatinized starch as binder/disintegrating agents in an IBU/APAP tablet, a series of prototype granulations, A-C (corn starch, microcrystalline cellulose) and D-F (pregelatinized starch), as shown on Table 2, were prepared by high-shear wet granulation with an HPMC binder solution; followed by drying in a GPGC-1 fluid bed dryer and milling with a hammer mill, number 1A screen (0.04 inch).

TABLE 2

Prototype formulations for IBU/APAP granulation and compressed tablet.

Corn Starch/Microcrystalline Cellulose Prototype Granulations.

| | Unit formula | | | | | |
|---|---|---|---|---|---|---|
| | A | | B | | C | |
| Ingredient | mg/unit | % | mg/unit | % | mg/unit | % |
| Ibuprofen | 200.00 | 26.67 | 200.00 | 27.16 | 200.00 | 27.67 |
| Acetaminophen | 325.00 | 43.33 | 325.00 | 44.13 | 325.00 | 44.96 |
| Hypromellose (E15) | 7.50 | 1.00 | 7.00 | 0.95 | 6.50 | 0.90 |
| Croscarmellose Sodium | 37.50 | 5.00 | 35.91 | 4.88 | 34.32 | 4.75 |
| Colloidal Silicon Dioxide | 15.00 | 2.00 | 14.36 | 1.95 | 13.73 | 1.90 |
| Corn Starch | 157.50 | 21.00 | 112.00 | 15.21 | 66.50 | 9.20 |
| Microcrystalline Cellulose | 0.00 | 0.00 | 34.77 | 4.72 | 69.53 | 9.62 |
| Purified Water | —[a] | —[a] | —[a] | —[a] | —[a] | —[a] |
| Glyceryl Behenate | 7.50 | 1.00 | 7.36 | 1.00 | 7.23 | 1.00 |
| Total | 750.00 | 100.00 | 736.40 | 100.00 | 722.81 | 100.00 |

TABLE 2-continued

Prototype formulations for IBU/APAP granulation and compressed tablet.

Pregelatinized Starch Prototype Granulations.

| | D | | E | | F | |
|---|---|---|---|---|---|---|
| | mg/unit | % | mg/unit | % | mg/unit | % |
| Ibuprofen | 200.00 | 26.67 | 200.00 | 28.57 | 200.00 | 30.77 |
| Acetaminophen | 325.00 | 43.33 | 325.00 | 46.43 | 325.00 | 50.00 |
| Hypromellose (E15) | 7.50 | 1.00 | 7.00 | 1.00 | 6.50 | 1.00 |
| Croscarmellose Sodium | 37.50 | 5.00 | 35.00 | 5.00 | 32.50 | 5.00 |
| Colloidal Silicon Dioxide | 15.00 | 2.00 | 14.00 | 2.00 | 13.00 | 2.00 |
| Pregelatinized Starch | 157.50 | 21.00 | 112.00 | 16.00 | 66.50 | 10.23 |
| Purified Water | —a | —a | —a | —a | —a | —a |
| Glyceryl Behenate | 7.50 | 1.00 | 7.00 | 1.00 | 6.50 | 1.00 |
| Total | 750.00 | 100.00 | 700.00 | 100.00 | 650.00 | 100.00 | aRemoved during processing

Results and Discussion.

Prototype A failed to form into granules and was compressed without milling; accordingly, Prototypes B-C were adjusted to also include microcrystalline cellulose.

Figure 1B:
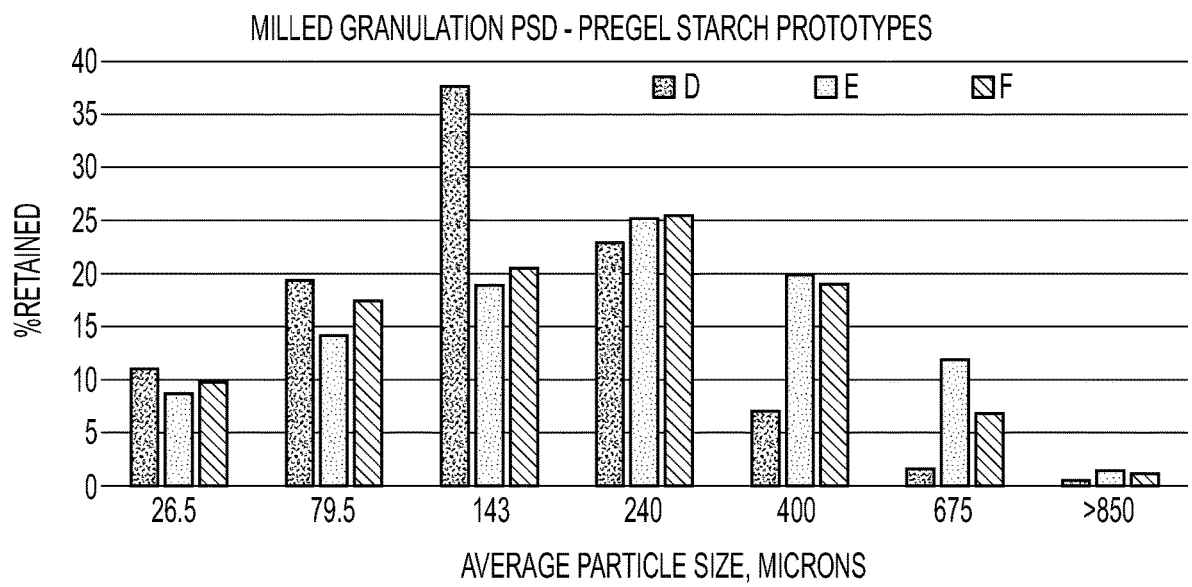

Particle size distribution. It was found that the particle size distribution (PSD) of the A-C granulations skewed toward finer particles with only minor levels of larger particles being formed, as shown on FIG. 1A. However, formulations with high levels of fines are not viable on high speed tablet presses because of poor flow and compression issues (for example, capping/lamination, picking/stick, weight variation, segregation). By comparison, the D-F granulations demonstrated superior granule formation with favorable PSD (FIG. 1B).

D50 refers to the mid-point in a particle size distribution such that half the particles in a population of granules are larger than the d50, and half are smaller. The d50 is the 50% midpoint for each curve in FIG. 2. Table 3 summarizes the d50's for each prototype granulation.

TABLE 3

Approximate d50, microns.

| Formulation | Approximate d50, microns |
|---|---|
| A | 71 |
| B | 64 |
| C | 51 |
| D | 110 |
| E | 171 |
| F | 151 |

The d50's of the corn starch granulations, A-C, are all <100 microns. By comparison, the pregelatinized starch formulas, D-F, have higher d50's of approximately 110 μm (D), 171 μm (E), and 151 μm (F).

Compression Results and Discussion

Compression studies were run on an instrumented table-top rotary tablet press equipped with capsule-shaped tooling. Force transducers captured the average main compression forces, no precompression force was used. Qualitative observations of powder flow during the compression runs were captured; powder flow for the pregelatinized starch blends (D-F) was significantly improved relative to the corn starch blends (A-C), and is consistent with the higher PSD of blends D-F.

Figure 3A:
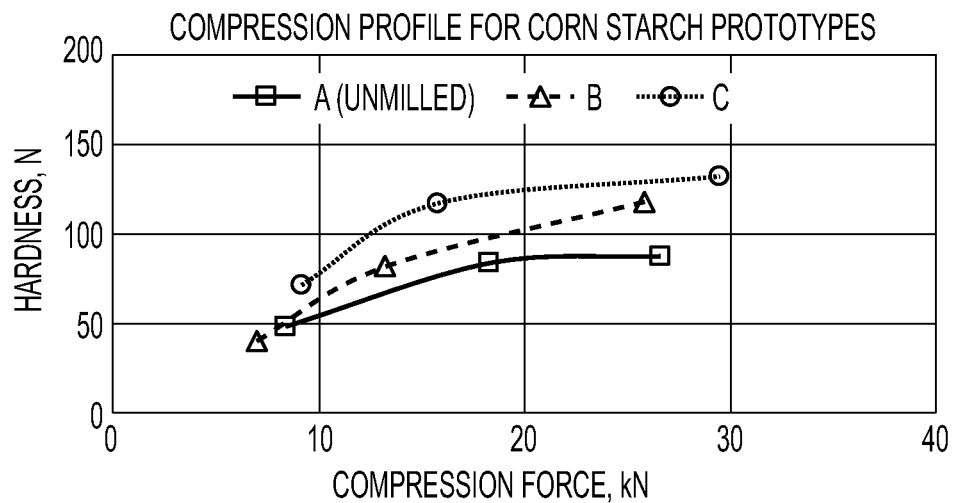
FIGS. 3A and 3B depict compression profiles for prototypes A-C and D-F, respectively. (Example 2)
Figure 3B:
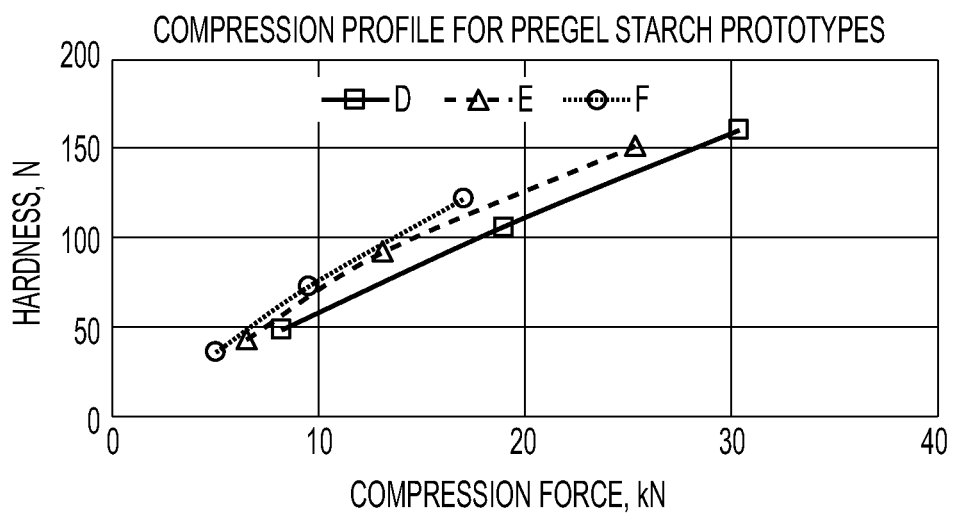

Compression profiles (compression force vs hardness) for B-F are shown in FIGS. 3A and 3B, respectively. The raw data for those figures is presented in Table 4.

TABLE 4

Compression Profile Data.

| Comp Force kN | Hardness N | Comp Force kN | Hardness N | Comp Force kN | Hardness N |
|---|---|---|---|---|---|
| A (unmilled) | | B | | C | |
| 8.4 | 48.35 | 7 | 40.21 | 9.2 | 70.90 |
| 18.3 | 83.85 | 13.2 | 81.59 | 15.8 | 116.50 |
| 26.6 | 87.77 | 25.8 | 117.97 | 29.5 | 131.61 |
| D | | E | | F | |
| 8.2 | 48.05 | 6.5 | 43.15 | 5 | 35.79 |
| 19 | 106.01 | 13.1 | 91.89 | 9.5 | 72.96 |
| 30.4 | 159.95 | 25.3 | 151.22 | 17 | 122.09 |

The corn starch prototypes, B and C, were found to have limited compression ranges, which in turn imposes limits on the compression force that may be applied to increase tablet hardness. Since compression profiles A-C tend to flatten out as the compression force is increased, application of compression force in the flattened range (referred to in the art as "capping limits") can result in capping, a tablet defect.

By comparison, the pregelatinized starch prototypes D-F all had significantly improved compression profiles relative to B-C. In the case of D-F, there was no indication of a capping limit; greater hardness was typically achieved with lower compression force; and all had wider compression windows, making them suitable for large-scale batch manufacturing.

Example 3. Embodiments of Manufacturing Process and Process Controls

Ibuprofen 125 mg/Acetaminophen 250 mg tablets can be manufactured by a process which includes wet granulation, optionally wet milling. drying, dry milling, blending, compression, film-coating and printing. The actual equipment and operating parameters are representative of those of a production batch and may vary based on the size of the batch; however, the operational and design class will remain the same.

The active pharmaceutical ingredients (API) Ibuprofen and APAP are known to be poorly compressible. In the exemplified product, API constitutes about 75% of the tablet weight (without coating). These characteristics must be accounted for, particularly to create a commercially viable composition that will withstand the manufacturing process. This will be particularly relevant in a large-scale batch manufacturing setting. Ibuprofen and acetaminophen can present challenges during multiple stages of the manufacturing process. First, ibuprofen has a relatively low melting point (75° C.-78° C.), so processing steps that expose the product to high temperature (e.g., drying and coating) should be minimized. Also, from a safety perspective, both ibuprofen and acetaminophen are known to give rise to concerns with explosivity during granulation and blending. Therefore, equipment must be properly grounded and the use of high-energy mills, such as hammer-mills, should be avoided unless they are operated under an inert atmosphere. Last, ibuprofen has a well-known tendency to adhere to tablet punch tooling faces, which can lead to tablet defects such as picking, sticking or filming. These defects are especially pronounced at lower tablet compression forces.

Exemplified batch formulae and sizes are reflected on Table 5.

TABLE 5

Embodiments of Large-Scale Batch Manufacturing of Ibuprofen 125 mg/Acetaminophen 250 mg Tablets.

| Names of Ingredients | Sub-Batch 650,000 Tablets Quantity (kg) | Small Batch 1,300,000 Tablets Quantity (kg) | Large Batch 3,900,000 Tablets Quantity (kg) |
|---|---|---|---|
| Tablet Core | | | |
| Ibuprofen | 81.25 | 162.50 | 487.50 |
| Acetaminophen | 162.50 | 325.00 | 975.00 |
| Hvoromellose (E15) | 4.88 | 9.76 | 29.28 |
| Croscarmellose Sodium | 21.61 | 43.22 | 129.66 |
| Colloidal Silicon Dioxide | 9.10 | 18.20 | 54.60 |
| Pregelatinized Starch (Corn) | 39.00 | 78.00 | 234.00 |
| Purified Water | —$^a$ | —$^a$ | —$^a$ |
| Glvcervl Dibehenate | 4.22 | 8.44 | 25.32 |
| Film Coat and Polish | | | |
| Opadrv II, Yellow | 12.50$^b$ | 25.00$^b$ | 75.00$^b$ |
| Purified Water | —$^a$ | —$^a$ | —$^a$ |
| Carnauba Wax #1 Yellow Powder | 0.0195 | 0.039 | 0.117 |
| Printing ink | | | |
| Opacode Black NS-78-17821 | 1.00$^c$ | 2.00$^c$ | 6.00$^c$ |
| Isopropyl Alcohol | —$^a$ | —$^a$ | —$^a$ |

$^a$Processing aid essentially removed during manufacturing.
$^b$Overage (~10%) is included to allow for system setup. Suspension prepared at a 20% solids concentration.
$^c$Excess is included for setup and refilling of ink into equipment
Note:
Two sub-batches of the final blend were used to produce the 1,300,000 tablet batch; and six sub-batches of the final blend were used to produce the 3,900,000 tablet batch.

Figure 7A:
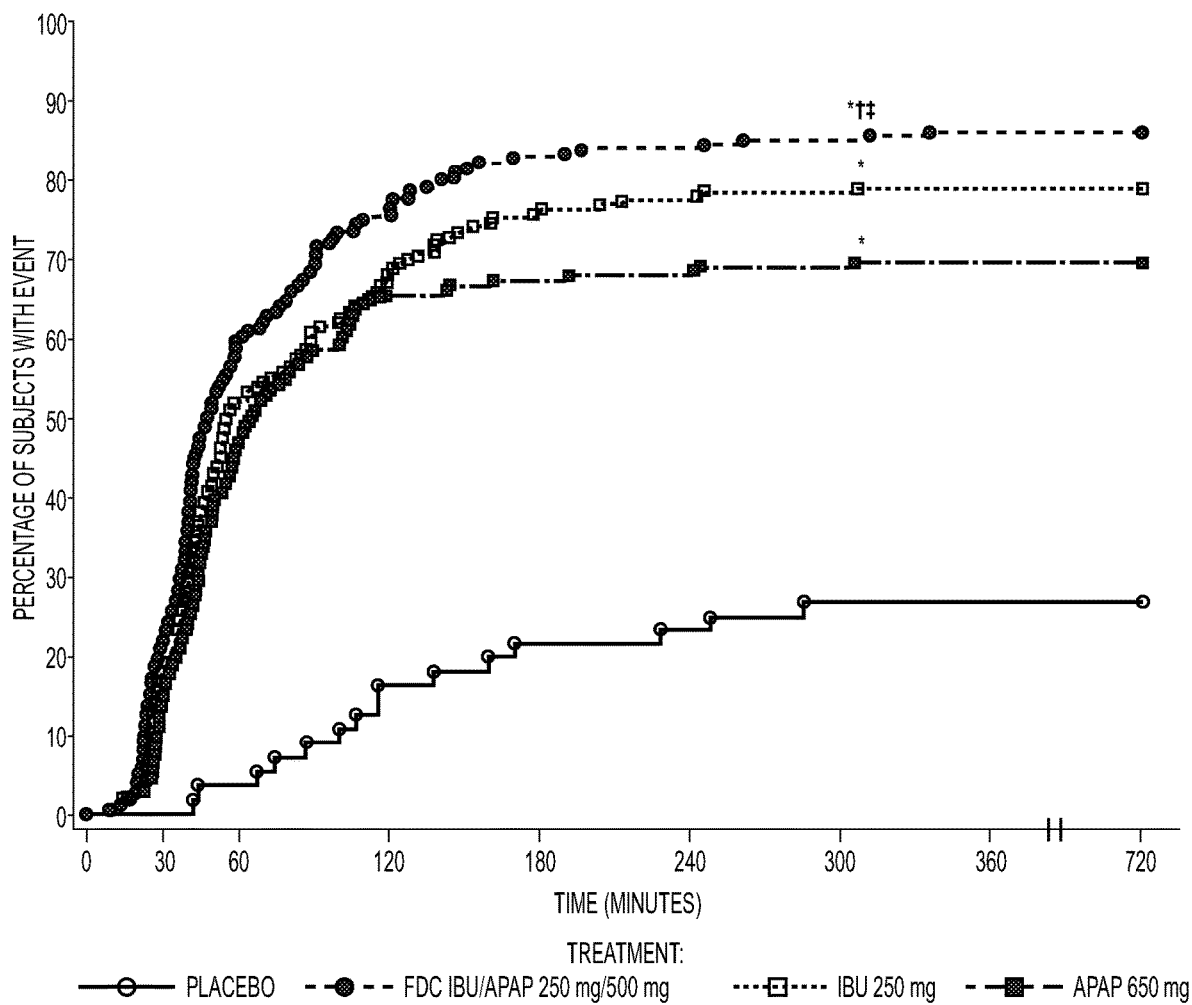
FIG. 7A shows Kaplan-Meier estimates of time to meaningful relief.
Figure 7B:
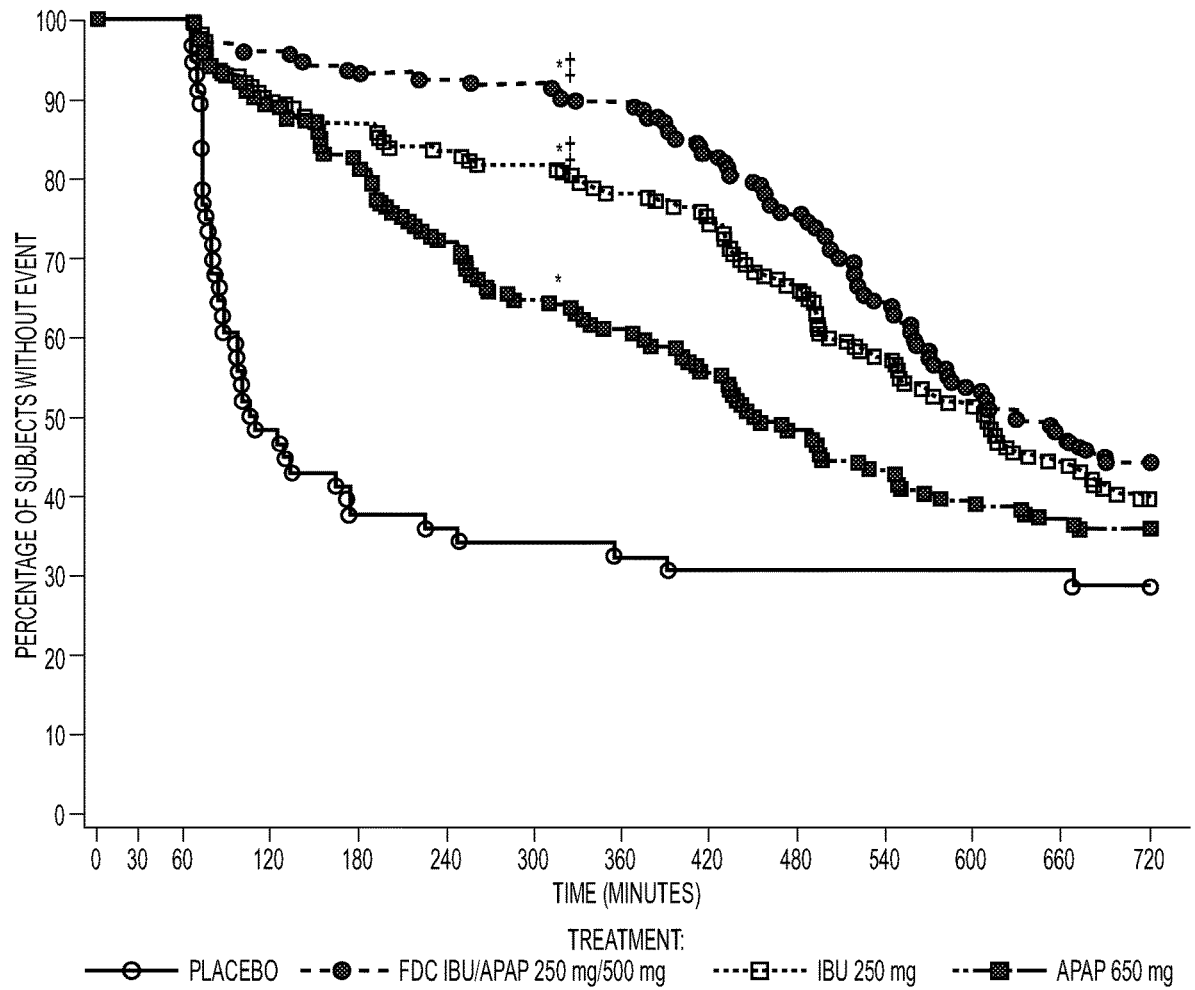
FIG. 7B shows Kaplan-Meier estimates of duration of pain relief, from Study 2. (Example 4c).

A flow diagram describing the exemplified commercial scale operations involved in the manufacture of Ibuprofen 125 mg/Acetaminophen 250 mg Tablets is shown in FIG. 7, which is a Flow Chart of Manufacturing Process for Ibuprofen 125 mg/Acetaminophen 250 mg Tablets.

Figure 4:
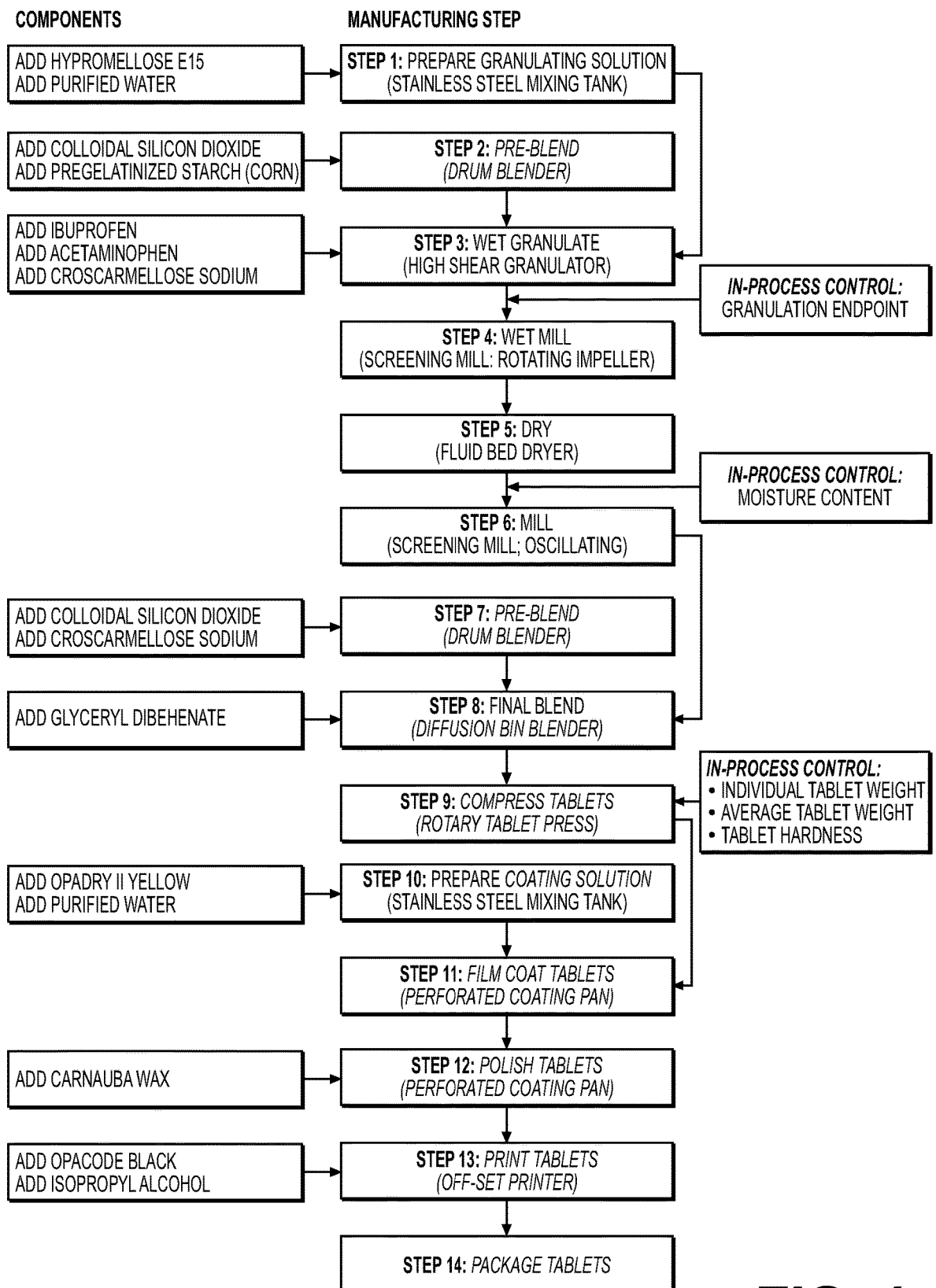
FIG. 4 is a flow chart of a manufacturing process for the exemplified Ibuprofen 125 mg/Acetaminophen 250 mg Tablet of Example 3.

As illustrated in FIG. 4, the steps of such a process are as follows:
1. Add hypromellose and purified water to a suitable stainless steel mixing tank equipped with a mixer. Mix until dissolved.
2. Add colloidal silicon dioxide and pregelatinized starch into a drum. blender. Blend for a minimum of two (2) minutes.
3. Add ibuprofen, pre-blend from Step 2, acetaminophen, and croscarmellose sodium through a sifter equipped with a #4 mesh stainless steel screen into a Wet High Shear Granulator. Dry mix on low speed for a minimum of two (2) minutes. Add the granulation solution from Step 1 and mix on low speed for a minimum of two (2) minutes. Increase speed to high and mix until granulation endpoint has been determined by the change in power consumption. The endpoint is achieved when: In-Process Control: Change in power consumption: 6 to 12 kW.
4. Wet milling. Pass the wet granulation through a Screening Mill (rotating impeller) fitted with a 0.25" screen directly into a Fluid Bed Dryer bowl.
5. Dry at an inlet air temperature set point of 55 to 65° C. and air flow between of 6000 to 8000 cfm. After twenty (20) minutes, adjust the air flow to 4600 to 6600 cfm. Dry until the exhaust air temperature reaches 32 to 52° C. Sample to determine moisture content by Karl Fischer. In-Process Control: The moisture content of the dried granulation should be not more than (NMT) 2.0% w/w. Note: If the moisture level is greater than 2.0% w/w, additional drying time may be applied.
6. Mill dried granulation from Step 5 using a Screening Mill (oscillating bar) equipped with a #16 mesh stainless steel screen directly into a Diffusion Bin Blender.
7. Add colloidal silicon dioxide and croscarmellose sodium into a drum blender. Blend for a minimum of two (2) minutes. Pass the pre-blend through a #20 mesh screen into an appropriate container.
8. Add pre-blend from Step 7 into Diffusion Bin Blender from Step 6. Add glyceryl dibehenate through a #20 mesh screen into the Diffusion Bin Blender. Blend for a minimum of nine (9) minutes. Discharge final blend into suitable containers.
9. Compress tablets on a Rotary Tablet Press (Gravity) with capsule-shaped tablet tooling (0.590"×0.291"×0.038"). The Tablet Press speed is set within a range of 30 to 55 rpm. In-Process Controls: Individual Tablet Weight: 471-521 mg; Average Tablet Weight (n=10): 486-506 mg; Tablet Hardness: 98-196 N.
10. Add the required amount of purified water and Opadry II Yellow to a suitable stainless steel mixing tank equipped with a mixer to prepare a 20% solids coating suspension. Mix until solids are dispersed.
11. Load tablet cores from Step 9 into Perforated Coating System. Perform the warm-up cycle until minimum required temperature is achieved. Dispense the appropriate amount of coating solution to achieve an approximate theoretical weight gain of 3%. After coating is complete, drop the inlet temperature and cool the coated tablets.
12. Dust the tablets with screened carnauba wax #1 yellow powder. After polishing is complete, discharge the coated tablets into appropriate container(s).
13. Print the tablets with pharmaceutical ink (Opacode Black NS-78-17821 diluted in isopropyl alcohol) using an Off-Set Printer.
14. Package the tablets in approved container closure system.

Testing of Composition Embodiments. Here we provide results from three studies of the compositions exemplified in Example 1.

Example 4a. Clinical Studies in Analgesic Efficacy—Study 1

The Study 1 objective was to determine the overall analgesic efficacy and tolerability of 3 different FDCs of IBU and APAP, each with a different amount of IBU, compared with IBU 400 mg, with a view toward demonstrating that the FDC IBU/APAP 250 mg/500 mg, administered as two tablets containing 125 mg ibuprofen, 250 mg acetaminophen (the tablets, for example as exemplified in Table 1 and manufactured as disclosed herein), is advantageous.

Study 1 was a phase 2, 12-hour, 5-arm, randomized, double-blind, parallel group, in-patient, placebo-controlled study designed to determine the overall analgesic efficacy of 3 different FDCs of IBU/APAP compared with IBU 400 mg and placebo.

All study procedures were in compliance with the ethical principles originating in or derived from the Declaration of Helsinki and with all International Council for Harmonization Good Clinical Practice Guidelines, as well as local regulatory requirements. All patients provided written informed consent. Eligible patients were healthy males or females aged 16-40 years, inclusive, who had undergone extraction of 3 third molar teeth (with at least 2 having been partial or complete bony mandibular impactions) and had developed at least moderate pain within 5 hours of the oral surgery. Other entry criteria included: use of only the following preoperative medications/anesthetics: topical benzocaine, a short-acting parenteral local anesthetic (mepivacaine or lidocaine) with or without a vasoconstrictor and/or nitrous oxide; no contraindications to the study or rescue medications; and being sufficiently reliable, cooperative, and intelligent to record the requested information on the analgesic questionnaire form.

Upon experiencing at least moderate pain, patients were randomized 1:3:3:3:3 to receive a single oral dose of placebo; IBU 400 mg; FDC IBU/APAP 200 mg/500 mg; FDC IBU/APAP 250 mg/500 mg; or FDC IBU/APAP 300 mg/500 mg.

Patients who did not experience adequate pain relief from study medication were permitted to take rescue medication, which consisted of either immediate-release tramadol, 50-100 mg. or codeine phosphate, 15-60 mg. Patients could receive 2 additional doses of rescue medication at the study center. Patients were permitted to take rescue medication at any time but were encouraged to wait at least 1 hour after taking study medication to allow time for the medication to exert its effect. Patients who took rescue medication remained at the study site for the full duration of the study and continued to perform assessments.

Study 1 Assessments and Endpoints.

At baseline, patients rated their pain severity using a categorical and a numerical pain severity rating (PSR) scale. The categorical PSR was a 4-point scale (none, mild, moderate, severe), with each category assigned a value from 0-3, respectively. The achievement of moderate pain at baseline was confirmed by a score of >50 mm on a 100-mm visual analog pain scale. Additionally, pain was assessed using an 11-point numerical PSR (0-10; 0=none to 10=worst possible pain).

Following the administration of study medication, patients were followed and evaluated on site for 12 hours. During that time, study participants provided self-ratings of pain severity (on both categorical and numerical PSR scales as described above) and pain relief: using a 5-point categorical pain relief rating (PRR) scale (0=none, 1=a little, 2=some, 3=a lot, and 4=complete) at 0.25, 0.5, 1, 1.5, 2, 3, 4, 5, 6, 7, 8, 9, 10, 11, and 12 hours post-treatment, after taking study medication, immediately before taking rescue medication, or at time of study withdrawal (if either occurred).

Additional patient assessments included time to first perceptible relief (TFPR) and time to meaningful pain relief (TMPR) using the double-stopwatch method, in which the first stopwatch was pressed by the patient when pain relief was first perceived, and the second when that relief became meaningful. Duration of pain relief was measured by the time to treatment failure (i.e., the time of first dose of rescue medication or dropout due to lack of efficacy). At 12 hours or immediately before taking rescue medication for the first time, patients also provided a Patient Global Evaluation based on a 6-point categorical scale ranging from 0 (very poor) to 5 (excellent).

The primary endpoint was the time-weighted sum of pain relief and pain intensity difference (PID) scores from baseline (time 0) through 8 hours ($SPRID[4]_{0-8}$) after dosing based on PRR and categorical PSR. Secondary endpoints included $SPRID[4]_{0-2}$, $SPRID[4]_{0-6}$, and $SPRID[4]_{0-12}$; TFPR and TMPR; cumulative proportion of patients attaining FPR and MPR by each time point; time-weighted sum of PRR scores over 0-2 hours ($TOTPAR_{0-2}$), 0-6 hours ($TOTPAR_{0-6}$), 0-8 hours ($TOTPAR_{0-8}$), and 0-12 hours ($TOTPAR_{0-12}$); time-weighted sum of categorical and numerical (PID) scores over the same intervals (SPID[4] and SPID[11]); duration of relief (as measured by time to treatment failure or patient discontinuation), cumulative proportion of treatment failures at each time point; and Patient Global Evaluation of study medication.

Patients were monitored for any AEs during the study. All AEs reported through 14 days after administration of study drug were reported regardless of relationship.

The primary analysis set (full analysis set) comprised all randomized patients who were dosed with study medication and who provided a baseline pain assessment. The safety analysis set comprised all patients who received at least 1 dose of study drug.

Based on results of a previous similarly designed study, it was expected that the difference in $SPRID[4]_{0-8}$ between the IBU 400 mg and any FDC group would be 5.9 units. Based on this assumption, a sample size of 90 patients per arm would give approximately 80% power to detect this difference in $SPRID[4]_{0-8}$ between treatments at the 5% level of significance (2-sided). All computations assumed a root mean square of error of 14.0 units (observed in previous study). Thus, a total of 390 patients were required to complete the study. Assuming a 5% dropout rate, a total of 410 patients were to be enrolled. Statistical comparisons between the individual FDCs were not made.

The PID (both scales), PRR, and their sum (PRID) at each time point, as well as the corresponding summary scales, SPID, TOTPAR, and SPRID, were analyzed by an analysis of variance model with treatment group, sex, baseline categorical PSR, and treatment-by-baseline categorical PSR interaction terms. For each comparison, the treatment difference based on the least squares mean and the associated P values were computed. The TMPR, TFPR, and time to treatment failure were analyzed using a proportional hazards regression model with terms for treatment, baseline categorical PSR, and sex. The 95% confidence intervals for each pairwise treatment difference were computed using the hazard ratio and associated 95% Wald confidence interval. The cumulative proportion of patients with MPR, FPR, complete relief, and treatment failure at each specified time point was compared via the Cochran-Mantel-Haenszel row mean score test, controlling for baseline categorical PSR and sex, using table scores. Patient global evaluation was analyzed using the Cochran-Mantel-Haenszel row mean score test, controlling for baseline categorical PSR and sex, using modified ridit scores.

All treatment differences were regarded as statistically significant at the P≤0.05 level (all tests were 2-sided) and declared marginally significant if 0.05<P≤0.10. As this was a proof-of-concept study, no adjustments for multiple comparisons were made.

Study 1 Results.

A total of 576 patients were screened, and 394 were randomized. Baseline characteristics within each of the treatment cohorts were well balanced between groups. Approximately 50% of patients were female, and the majority (>95%) were white; the mean age was 18.1 years. Overall, 61.9% of patients ranked their pain on study entry as severe on the categorical PSR scale.

Study 1—Efficacy.

Figure 5:
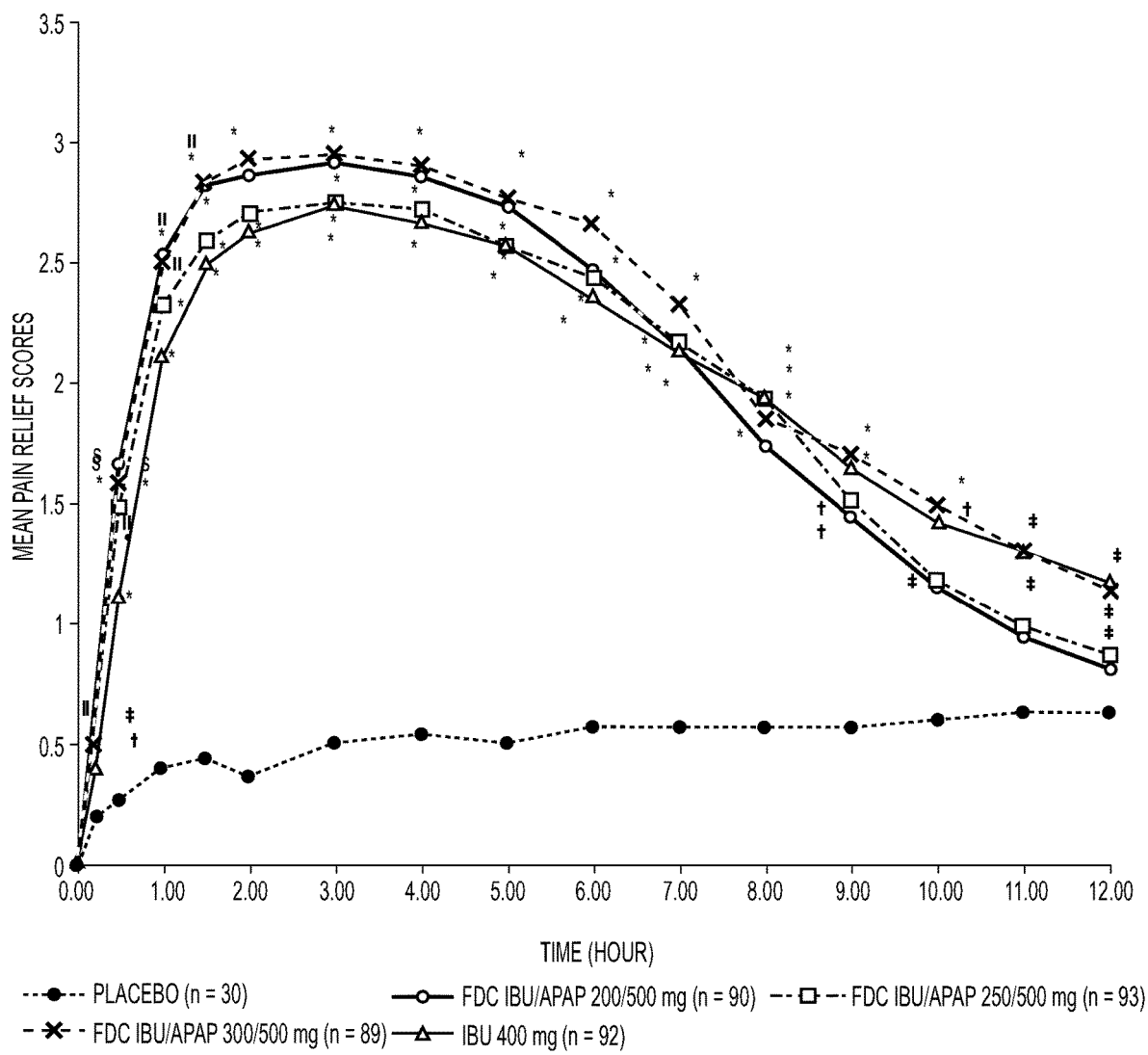
FIG. 5 summarizes the Study 1 course of pain relief over time with the fixed-dose combination (FDC) of IBU 200 mg with APAP 500 mg; IBU 250 mg with APAP 500 mg; IBU 300 mg with APAP 500 mg; IBU 400 mg; and placebo (Example 4a)

The course of pain relief over time with the FDCs, IBU 400 mg and placebo is illustrated in FIG. 5 (*P≤0.001 vs placebo; †P≤0.01 vs placebo; ‡P≤0.05 vs placebo; § P≤0.01 vs IBU 400 mg; ||P≤0.05 vs IBU 400 mg; ¶P≤0.05 vs FDC IBU/APAP 200 mg/500 mg).

Significantly better pain relief was observed with all FDC formulations versus placebo from the 0.25-hour time point through the 10- or 11-hour time points, whereas IBU 400 mg was significantly better than placebo from 0.50 hour to the end of the study. The FDC formulations provided significantly better pain relief than IBU 400 mg at earlier time points, but IBU 400 mg trended better than some of the FDC formulations, with several of these differences achieving statistical significance.

All active treatments were significantly superior to placebo for the primary end-point of SPRID[4]$_{0-8}$ (P<0.001 for all comparisons). There was no significant difference between any of the FDC formulations and IBU 400 mg for the primary endpoint.

A similar result was seen for the secondary endpoints of SPRID[4]$_{0-2}$, SPRID [4]$_{0-6}$, and SPRID[4]$_{0-12}$. However, FDC IBU/APAP 200 mg/500 mg and FDC IBU/APAP 300 mg/500 mg were significantly better than IBU 400 mg for SPRID[4]$_{0-2}$ (P<0.05). Similar patterns were seen for time-weighted SPID[4] and SPID[11] scores over the same time intervals (data not shown).

All active treatment groups delivered significantly better pain relief, as measured by TOTPAR, than placebo for all comparisons (Table 6). In addition, FDC IBU/APAP 200 mg/500 mg and FDC IBU/APAP 300 mg/500 mg provided superior pain relief relative to IBU 400 mg for the 0-2 hour interval (TOTPAR$_{0-2}$; P=0.031 and P=0.011, respectively).

TFPR with the IBU/APAP FDCs ranged from 18.5-22.8 minutes compared with 24.9 minutes with IBU 400 mg and >720 minutes with placebo (Table 7). TFPR was significantly faster (P<0.001) with all active treatment groups versus placebo.

Additionally, FDC IBU/APAP 200 mg/500 mg and FDC IBU/APAP 300 mg/500 mg had significantly faster TFPR than IBU 400 mg (P=0.012 and P=0.030, respectively). Significantly higher percentages of patients reported FPR versus placebo from the first evaluation point at 0.25 hours (P=0.031) through the end of the study (P<0.001 for all time points from 0.5-12 hours).

The median TMPR with the FDC IBU/APAP formulations ranged from 44.5-54.1 minutes compared with 56.2 minutes with IBU 400 mg and >720 minutes with placebo (Table 5). All of the active treatment regimens provided significantly faster TMPR than placebo (P<0.001). FDC IBU/APAP 200 mg/500 mg also had significantly faster median TMPR than IBU 400 mg (44.5 min vs 56.2 min; P=0.014); the other FDCs did not reach statistical significance for this comparison. The median time to treatment failure with placebo was 1.6 hours, whereas the median time to treatment failure with FDC IBU/APAP 200 mg/500 mg; FDC IBU/APAP 250 mg/500 mg; and FDC IBU/APAP 300 mg/500 mg was 9.7 hours, 10.1 hours, and 11.1 hours, respectively. Results for the FDCs were not significantly different from IBU 400 mg (10.4 hours; Table 7).

For Patient Global Evaluation, all of the FDC formulations and IBU 400 mg yielded significantly better scores than placebo (P<0.001 for all comparisons), but there was no significant difference between any of the FDCs and IBU 400 mg.

Study 1—Safety.

The overall incidence of AEs was comparable among all treatment groups, with no significant differences seen for any system organ class. A total of 256 treatment-emergent AEs were reported by 127 patients (32.2%). The majority of AEs were mild or moderate in severity, and none were determined to be treatment related. There were no serious AEs. Nausea, vomiting and dizziness were the most commonly reported AEs (Table 8). The incidence of nausea was greater in the placebo group relative to the active treatment groups. There were no differences observed between the FDC groups and the IBU 400 mg group. Two patients, one each in the FDC IBU/APAP 200 mg/500 mg and FDC IBU/APAP 250 mg/500 mg groups, discontinued due to vomiting within 1 hour of taking study medication; both events were considered related to the surgical procedure rather than treatment.

Study 1—Discussion.

This dose-ranging study demonstrated that FDCs of IBU and APAP (200 mg/500 mg; 250 mg/500 mg; and 300 mg/500 mg) provided significantly better pain relief over 8 hours than placebo and were comparable to IBU 400 mg. There was also no difference between the FDCs and IBU 400 mg over 0-6 and 0-12 hours. However, each of the FDC doses showed significantly better pain relief at 30 minutes post-dose (all P≤0.01) than IBU 400 mg, suggesting a faster onset of action.

Figure 2:
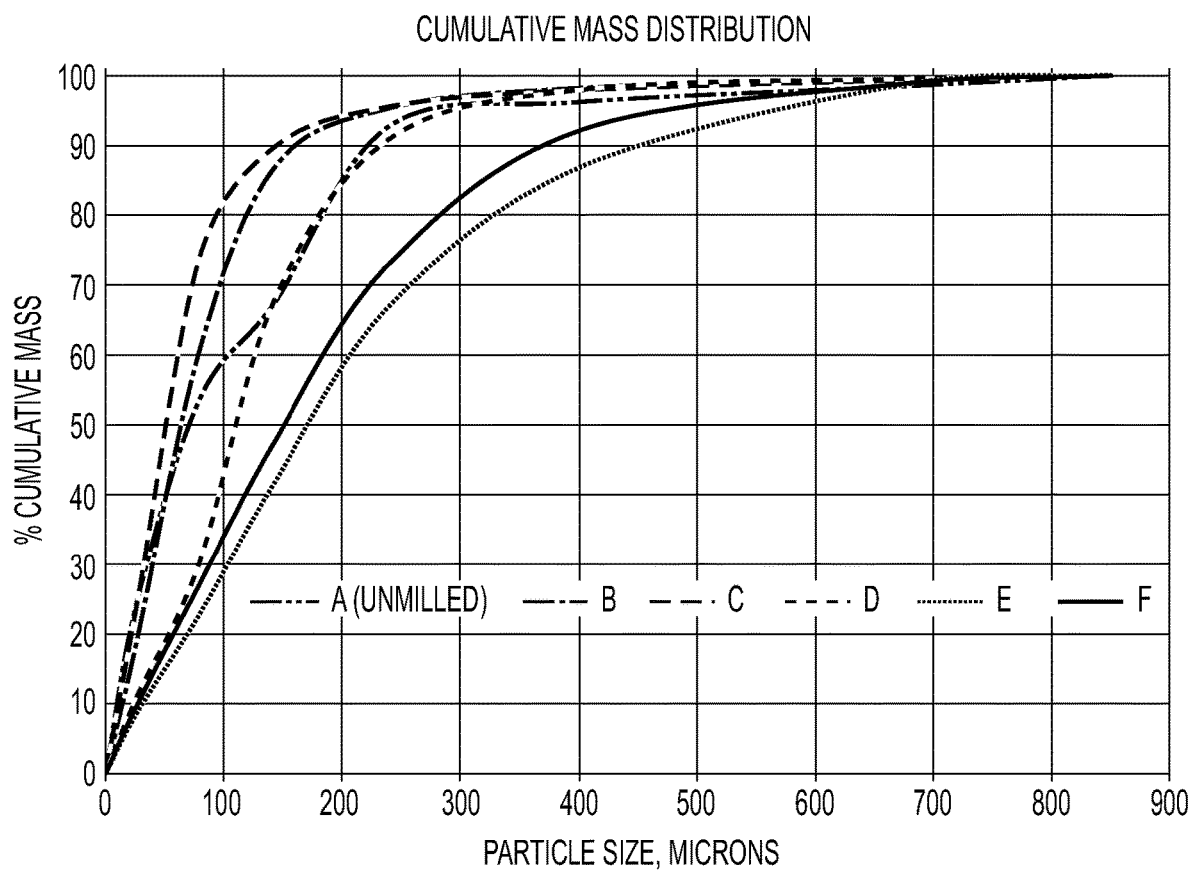
FIG. 2 is a graph showing the cumulative mass distribution for prototype formulations A-F (Example 2).

TMPR and duration of relief are other important metrics for acute analgesics. The time to onset of pain relief was significantly faster with the FDCs than with placebo. There was also a trend toward faster TMPR relative to IBU 400 mg alone, but this reached statistical significance only with FDC IBU/APAP 200 mg/500 mg (44.5 min vs 56.2 min; P=0.014). This faster TMPR seen with the FDC is consistent with that seen in previous dental pain studies in which FDC IBU/APAP 200 mg/500 mg was compared with IBU 400 mg. The statistically significant difference in pain relief between FDC IBU/APAP 200 mg/500 mg and IBU 400 mg, and between FDC IBU/APAP 300 mg/500 mg and IBU 400 mg, for the TOTPAR$_{0-2}$ interval further supported the faster onset of action; FDC IBU/APAP 250 mg/500 mg did not reach statistical significance versus IBU 400 mg but showed a similar trend. This is perhaps to be expected, as an APAP tablet has a faster time to maximum concentration than IBU. TFPR followed a similar pattern. Another trend, based on the data as shown in FIG. 2, was that FDC IBU/APAP 250 mg/500 mg surprisingly showed the highest mean pain relief score at 8 hours comparatively.

The duration of relief, as measured by time to treatment failure, was significantly longer with the FDCs than with placebo. There was no significant difference between the FDCs and IBU 400 mg; however, the duration of action increased directionally with the amount of IBU in the combination.

The most frequent AEs were nausea, vomiting and dizziness. These AEs are commonly encountered following removal of wisdom teeth and may be related to the surgical procedure and/or anesthesia. These AEs occurred most frequently in the placebo group and may have been due to greater pain and use of opioid rescue medications in this group. Overall, the AE profile of the FDCs was comparable to IBU 400 mg and placebo. There were no unexpected AEs, and the safety profile of the FDCs was consistent with that seen in previous studies.

This study demonstrates that all 3 FDCs of IBU/APAP had efficacy comparable to IBU 400 mg for the majority of primary and secondary efficacy endpoints, with a similar safety profile.

However, there was some suggestion that the FDC may have a more rapid onset of action than IBU alone. Overall, since none of the combinations were substantially different from one another or from IBU 400 mg conclusions cannot be drawn from this study as to which FDC dose combination is superior. However, it can be concluded that the FDCs of IBU and APAP evaluated in this study provide pain relief at least as effectively as IBU 400 mg with a lower exposure than with the maximum OTC doses of IBU (400 mg) and APAP (1000 mg). Since multiple studies have demonstrated that IBU 400 mg is superior to APAP 1000 mg and previous studies demonstrated that FDC IBU/APAP 200 mg/500 mg was superior to APAP 1000 mg, all of the FDCs evaluated herein would also be expected to be superior to the maximal dose of APAP.

TABLE 6

Summary of Time-Weighted Pain Relief Rating Scores.

| TOTPAR, mean (SD) | Placebo (n = 30) | FDC IBU/APAP 200 mg/500 mg (n = 90) | FDC IBU/APAP 250 mg/500 mg (n = 93) | FDC IBU/APAP 300 mg/500 mg (n = 89) | IBU 400 mg (n = 92) |
|---|---|---|---|---|---|
| $TOTPAR_{0-2}$ | 0.7 (1.1) | 4.7 (1.7)*† | 4.3 (1.9)* | 4.7 (1.8)*‡ | 4.0 (1.8)* |
| $TOTPAR_{0-6}$ | 2.8 (5.4) | 15.7 (5.2)* | 14.8 (6.5)* | 16.0 (6.3)* | 14.3 (6.7)* |
| $TOTPAR_{0-8}$ | 4.0 (7.6) | 19.6 (7.2)* | 18.9 (8.8)* | 20.2 (8.6)* | 18.4 (9.2)* |
| $TOTPAR_{0-12}$ | 6.4 (12.6) | 23.9 (11.2)* | 23.4 (12.6)* | 25.8 (12.9)* | 23.9 (13.8)* |

*$P < 0.001$ vs placebo;
†$P = 0.031$ vs IBU 400 mg;
‡$P = 0.011$ vs IBU 400 mg.

TABLE 7

Time to Meaningful Relief, First Perceptible Relief, and Treatment Failure.

| Median time to . . . | Placebo (n = 30) | FDC IBU/APAP 200 mg/500 mg (n = 90) | FDC IBU/APAP 250 mg/500 mg (n = 93) | FDC IBU/APAP 300 mg/500 mg (n = 89) | IBU 400 mg (n = 92) |
|---|---|---|---|---|---|
| Meaningful relief, min | >720 | 445*,† | 54.1* | 45.9* | 56.2* |
| First perceptible relief, min | >720 | 18.5*‡ | 22.8* | 18.5*§ | 24.9* |
| Treatment failure, hour | 1.6 | 9.7* | 10.1* | 11.1* | 10.4* |

*$P < 0.001$ vs placebo;
†$P = 0.014$ vs IBU 400 mg;
‡$P = 0.012$ vs IBU 400 mg;
§$P = 0.030$ vs IBU 400 mg.

TABLE 8

Summary of Treatment-Emergent Adverse Events Occurring in ≥3 Patients in Any Treatment Arm.

| Adverse event, n (%) | Placebo (n = 30) | FDC IBU/APAP 200 mg/500 mg (n = 90) | FDC IBU/APAP 250 mg/500 mg (n = 93) | FDC IBU/APAP 300 mg/500 mg (n = 89) | IBU 400 mg (n = 92) |
|---|---|---|---|---|---|
| Nausea | 14 (46.7) | 22 (24.4) | 18 (19.4) | 16 (18.0) | 22 (23.9) |
| Vomiting | 7 (23.3) | 8 (8.9) | 11 (11.8) | 5 (5.6) | 14 (15.2) |
| Alveolar osteitis | 0 | 4 (4.4) | 2 (2.2) | 1 (1.1) | 2 (2.2) |

TABLE 8-continued

Summary of Treatment-Emergent Adverse Events
Occurring in ≥3 Patients in Any Treatment Arm.

| Adverse event, n (%) | Placebo (n = 30) | FDC IBU/APAP 200 mg/500 mg (n = 90) | FDC IBU/APAP 250 mg/500 mg (n = 93) | FDC IBU/APAP 300 mg/500 mg (n = 89) | IBU 400 mg (n = 92) |
|---|---|---|---|---|---|
| Dizziness | 3 (10.0) | 9 (10.0) | 6 (6.5) | 7 (7.9) | 7 (7.6) |
| Tension headache | 0 | 4 (4.4) | 1 (1.1) | 1 (1.1) | 4 (4.3) |
| Tremor | 1 (3.3) | 1 (1.1) | 2 (2.2) | 3 (3.4) | 2 (2.2) |
| Paresthesia | 1 (3.3) | 0 | 0 | 0 | 0 |
| Feeling hot | 2 (6.7) | 4 (4.4) | 1 (1.1) | 4 (4.5) | 4 (4.3) |
| Muscular weakness | 1 (3.3) | 0 | 0 | 0 | 0 |
| Post procedural hemorrhage | 0 | 0 | 2 (2.2) | 3 (3.4) | 0 |

The proposed dosing regimen for the FDC IBU/APAP 250 mg/500 mg is every 8 hours (TID), resulting in a total daily IBU dose of 750 mg and a total daily APAP dose of 1500 mg both of which are considerably lower than the currently approved over-the-counter (OTC) maximum daily doses for the agents (1200 mg and 4000 mg, respectively).

Example 4b-c. Clinical Studies in Analgesic Efficacy—Studies 2 and 3

Two additional studies (Studies 2 and 3) were performed demonstrating the performance of compositions contemplated by the Inventors. The objectives of the two studies described herein were to determine if:
1) the FDC IBU/APAP 250 mg/500 mg provided superior analgesia to its individual components (Study 2);
2) the FDC had a rapid onset of analgesia (within 1 hour) (Studies 2 and 3);
3) the 8-hour dosing interval was appropriate (Studies 2 and 3); and
4) analgesic efficacy was sustained with multiple doses (Study 3).

Two Studies were performed, both single-center, phase 3, randomized, double-blind, parallel-group, placebo-controlled studies conducted in the United States. Study 2 was a single-dose study whereas Study 3 was a multiple-dose study. The studies were performed in compliance with the ethical principles originating in or derived from the Declaration of Helsinki and in compliance with all International Council for Harmonization Good Clinical Practice Guidelines, as well as all local regulatory requirements.

In Study 2, patients experiencing moderate-severe pain after ≥3 third molar extractions, with at least 2 with partial or complete mandibular impaction, were randomized 3:3:3:1 to receive single-dose FDC IBU/APAP 250 mg/500 mg (administered as 2 tablets of IBU 125 mg/APAP 250 mg), IBU 250 mg alone, APAP 650 mg alone, or placebo under double-blind conditions. Patients self-assessed pain severity and pain relief on site for 12 hours following administration of study medication.

Study 3 had a similar design except that it was a multiple-dose trial. Patients with at least moderate pain following extraction of ≥3 third molars, with at least 2 with partial or complete mandibular impaction, were randomized 2:1 to receive FDC IBU/APAP 250 mg/500 mg or placebo. Patients received study drug every 8 hours for 40 hours and self-assessed pain severity and relief up to 48 hours posttreatment.

In both studies 2 and 3, patients who did not experience adequate pain relief were permitted to take rescue medication. Rescue medication consisted of tramadol hydrochloride 50-100 mg or codeine sulfate 15-60 mg, both immediate release, and patients could administer additional doses every 4-6 hours as needed up to the maximum labeled daily dose. Patients who took rescue medication remained at the study site for the full duration of each study (12 or 48 hours, respectively) and continued to perform assessments.

Studies 2 and 3—Patients.

In both studies 2 and 3, patients were healthy adult males or females aged 18-40 years inclusive, who had undergone surgical extraction of ≥3 third molar teeth (≥2 must have been partial or complete bony mandibular impactions). Other key entry criteria included moderate-severe pain confirmed by a rating of ≥50 mm on a 100-mm visual analog pain severity rating (PSR) scale within approximately 5 hours after completion of surgery and use of only the following preoperative medications/anesthetics: topical benzocaine, a short-acting parenteral local anesthetic (mepivacaine or lidocaine) with or -without a vasoconstrictor and/or nitrous oxide, and no contraindications to the study or rescue medications.

In Study 2, enrolled patients received one of 4 treatments: 1) placebo (administered as 2 tablets); 2) FDC IBU/APAP 250 mg/500 mg (administered as 2 caplets of IBU 125 mg/APAP 250 mg); 3) IBU 250 mg (administered as 2 caplets of IBU 125 mg); or APAP 650 mg (administered as 2 tablets of APAP 325 mg).

In Study 3, enrolled patients received one of 2 treatments: 1) placebo (administered as 2 tablets) or 2) FDC IBU/APAP 250 mg/500 mg (administered as 2 tablets of 1BU 125 mg/APAP 250 mg). All patients in both studies received 2 tablets of study medication under double-blinded conditions. Patients were blindfolded during study drug administration, which was performed by study site personnel not involved in any other aspects of the studies.

Study 2 and 3—Assessments and Endpoints.

At baseline, patients provided self-ratings of pain severity using categorical and numerical PSR scales. The categorical PSR used a 4-point scale (none, mild, moderate, severe), with each category assigned a number from 0 (none) to 3 (severe). Patients reporting at least moderate pain on the categorical PSR at baseline completed a 100-mm visual analog scale. A score of at least 50 mm confirmed eligibility for the study. Additionally, an 11-point (0-10; 0=none to 10=worst possible pain) numerical PSR scale was also used to assess pain.

Once study treatment was administered, the categorical PSR, numerical PSR, and a 5-point categorical pain relief rating scale (0=none, 1=a little, 2=some, 3=a lot, 4=complete) were obtained at predefined assessment times to assess pain and pain relief. In Study 2 (single-dose trial), these assessments were performed at 0.25, 0.5, 1, 1.5, 2, 3, 4, 5, 6, 7, 8, 9, 10, 11, and 12 hours post-treatment. In Study 3 (multiple-dose trial), these assessments were performed at the same time points as in Study 2 up to 12 hours and also at 16, 24, 32, 40, and 48 hours post-treatment Additional evaluations included patient assessments of time to first perceptible pain relief (TFPR), defined as the time that a patient first began to feel any pain-relieving effect whatsoever of the drug and time to meaningful pain relief (TMPR), defined as the time that a patient experienced pain relief that was meaningful to that individual, using the double-stopwatch method, see Mehlisch D R et al., 2010, ibid. In Study 2, these assessments were done over the 12-hour study period or until the first use of rescue medication; in Study 3, stopwatch assessments were performed over the first 8 hours after the initial dose of study medication up to the time of the second dose or first use of rescue medication, whichever occurred first. In both studies, a Patient Global Evaluation asked patients to rate the study medication as a pain reliever on a 6-point categorical scale ranging from 0 (very poor) to 5 (excellent). This evaluation was completed at the end of Study 2 (12 hours), at 24 and 48 hours in Study 3, or immediately before first rescue medication administration (if applicable) in both studies.

The pain intensity difference (PID[11]) at each time point was derived by subtracting the numerical PSR at that time point from the numerical PSR at baseline. The primary endpoint in Study 2 was the time-weighted sum of PID[11] scores based on the 11-point numerical PSR scale during the interval from baseline to 8 hours (SPID[11]$_{0-8}$. Other endpoints included the time-weighted sum of PID[11] scores from 6-8 hours (SPID[11]6-8), the time-weighted sum of pain relief rating scores over 0-8 hours and 6-8 hours (TOTPAR$_{0-8}$ and TOTPAR$_{6-8}$), TFPR (confirmed by TMPR), TMPR, duration of pain relief (as measured by time to treatment failure (defined as the time to first rescue medication use or dropout due to AE or lack of efficacy), the cumulative proportion of treatment failures at 6 and 8 hours, and the Patient Global Evaluation score.

In the multiple-dose Study 3, the primary endpoint was the time-weighted sum of PID[11] scores based on the 11-point numerical PSR scale from 0-24 hours (SPID[11]$_{0-24}$). Other endpoints included SPID[11]$_{0-8}$, SPID [11]$_{6-8}$, the time-weighted sum of PID[11] scores from 0-16 hours (SPID[11]$_{0-16}$), the time-weighted sum of PID[11] scores from 8-16 hours (SPID[11]$_{8-16}$), the time-weighted sum of PID[11] scores from 0-48 hours (SPID[11]$_{0-48}$), TFPR, TMPR, the duration of pain relief after the first dose (time to first use of rescue medication or second dose of study medication, or dropout due to AE or lack of efficacy), proportion of treatment failures within the first dosing (0-8 hours) interval and overall (0-48 hours), and Patient Global Evaluation of study drug. In both studies, patients were closely monitored for any AEs during surgery and the pain assessment period. AEs were recorded as they occurred or were reported.

Studies 2 and 3—Statistics.

For Study 2, a sample size of 168 patients in each active treatment group and 56 in the placebo group was estimated to provide at least 85% power (at the 5% significance level, 2-sided) to detect a difference of 6.1 and 7.9 in SPID[11]$_{0-8}$ between the FDC formulation treatment group and the IBU 250 mg and APAP 650 mg treatment groups, respectively, and a difference of 8.5 between the FDC formulation and placebo. These differences assumed a root mean square of error (RMSE) of 18.26 for SPID[11]$_{0-8}$. Allowing for a 5% dropout rate, approximately 588 patients were to been rolled.

For Study 3, a sample size of 68 patients for the FDC formulation treatment group and 34 patients for the placebo group was estimated to provide at least 85% power (at the 5% significance level, 2-sided) to detect a difference of at least 33 in SPID[11]$_{0-24}$. This assumed an RMSE of approximately 52 for SPID[11]$_{0-24}$, which was estimated based on the RMSEs for SPID[11] over 2, 8, and 12 hours. Assuming a 10% dropout rate, approximately 112 patients were to be enrolled. Assumptions for the sample size calculations for both studies were based on data from the single-dose pilot dental pain study.

SPID endpoints in both studies were analyzed using an analysis of covariance model with treatment group, sex, and baseline categorical and numerical PSR in the model. For each comparison, the treatment difference based on the least squares mean and the P value and associated 95% confidence interval based on the main model are presented.

The duration of pain relief, TFPR, and TMPR were analyzed using the Gehan-Wilcoxon test with effects for treatment, sex, and baseline categorical PSR asterms. These endpoints (except TFPR) are displayed graphically using the survival curves based on the Kaplan-Meier estimates. The median survival time and its corresponding 95% CI are presented and were estimated using the method of Simon and Lee (Simon R and Lee Y J, "Nonparametric confidence limits for survival probabilities and median survival time,". *Cancer Treat Rep.* 1982; 66:37-42), TOTPAR was analyzed using a main effects analysis of variance model with treatment, baseline categorical PSR, and sex terms in the model.

The cumulative proportions of treatment failures at 6 and 8 hours post dose in Study 2 and the proportions of treatment failures across the first dosing interval (0-8 hours) and overall (0-48 hours) in Study 3 were analyzed with the Cochran-Mantel-Haenszel (CMH) general association test controlling for baseline categorical PSR and sex, using table scores. Patient Global Evaluation in both studies was analyzed using a CMH row mean score test, stratifying by sex and baseline categorical PSR using modified ridit scores.

To protect the primary endpoint in Study 2 against a type I error due to multiple comparisons, 2-sided treatment group comparisons at the 5% significance were conducted in the following order: FDC versus placebo, FDC versus IBU and FDC versus APAP, IBU versus placebo, APAP versus placebo, and IBU versus APAP.

Studies 2 and 3—Results.

Participants and Baseline Characteristics.

A total of 722 patients were screened and 568 randomized in Study 2, and a total of 203 were screened and 123 randomized in Study 3. Baseline characteristics within each of studies 2 and 3 were well balanced between treatment groups. In both studies, approximately 40% to 45% of patients were male and the majority (>90%) were white. The mean age was 19.5 and 21.8 years in Study 2 and 3, respectively. Based on the 4-point categorical PSR scale, 44.9% had moderate pain and 55.1% had severe pain at baseline in Study 2, while 53.7% of patients had moderate pain and 46.3% had severe pain at baseline in Study 3.

Efficacy: Single-Dose Study 2.

Figure 6:
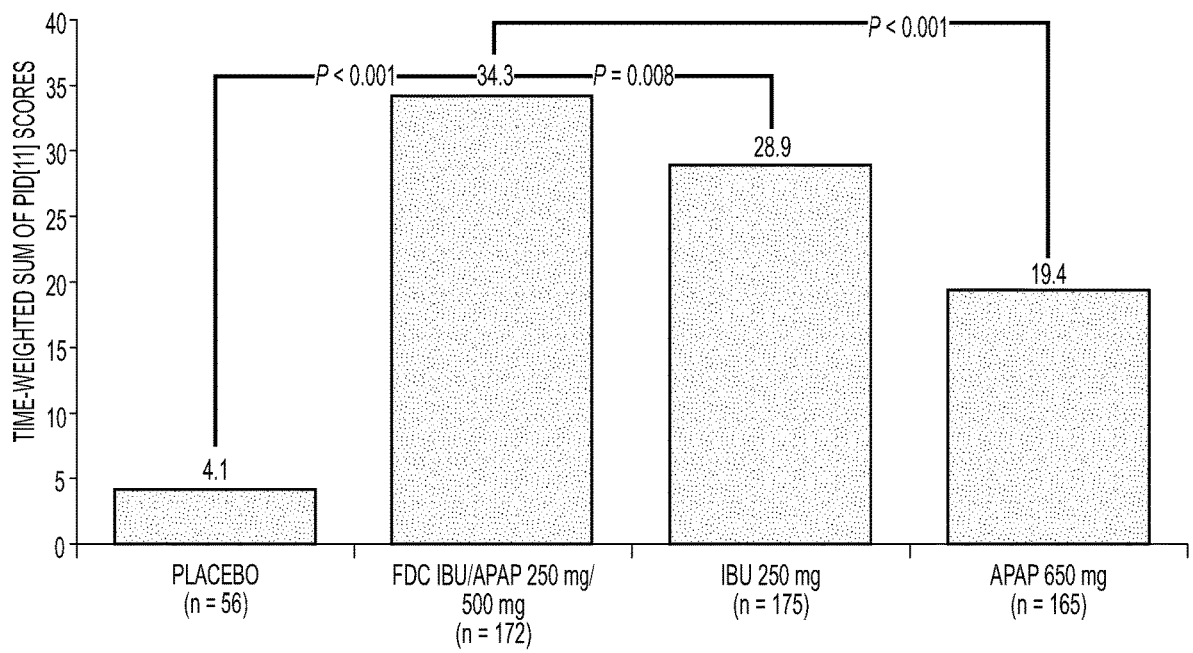
FIG. 6 shows SPID$[11]_{0-8}$ scores from single-dose Study 2 (Example 4b).

FIG. 6 shows SPID[11]$_{0-8}$ scores from Study 2. The single-dose study met its primary endpoint: FDC IBU/APAP 250 mg/500 mg was significantly better for SPID[11]$_{0-8}$ than placebo, IBU alone, and APAP alone (P<0.001, P=0.008, and P<0.001, respectively; Table 7). The FDC was also significantly better than both placebo and APAP alone for SPID[11] 6-8 (both, P<0.001), but this difference was not statistically significant for SPID[11]$_{6-8}$ for the FDC compared with IBU alone (P=0.053). FIG. 6 shows time-weighted sum of PID[11] scores from time 0 to 8 hours (SPID[11]$_{0-8}$) in single-dose Study 2.

Figure 8:
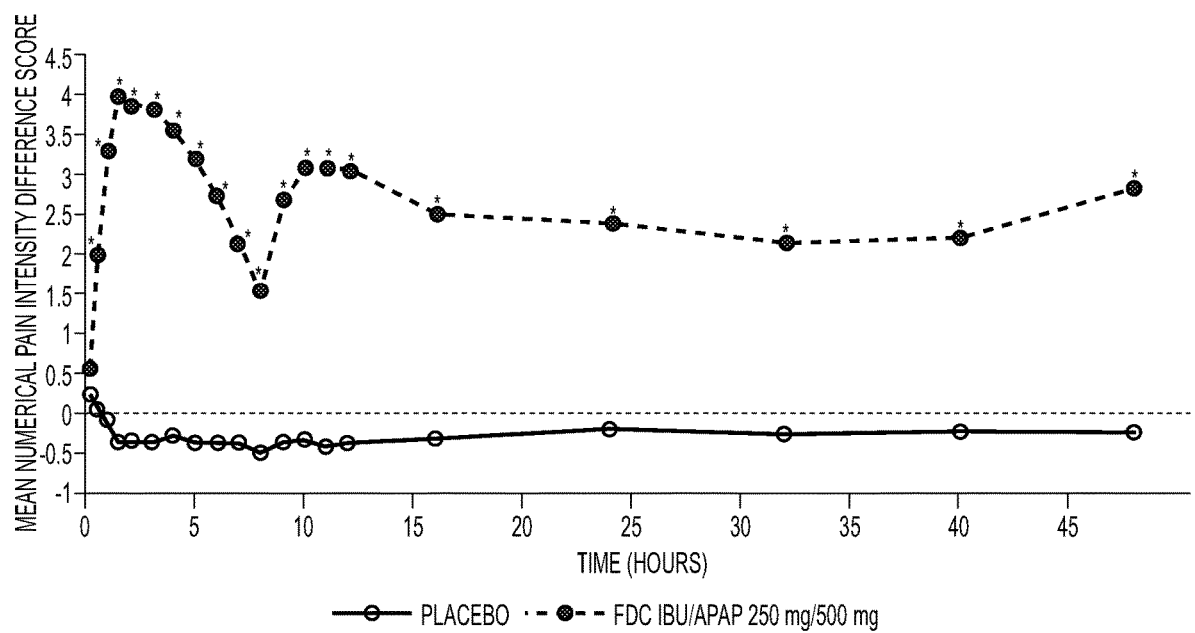
FIG. 8 shows numerical pain intensity difference scores over time from multiple-dose Study 3 (Example 4c).

FIGS. 8A and 8B respectively show Kaplan-Meier estimates of 1) time to meaningful relief and 2) duration of pain relief in the single-dose Study 2. Time to meaningful relief was measured from time of dosing until the patient depressed a second stopwatch to indicate meaningful relief had been achieved. Duration of pain relief was defined as time to treatment failure, which was measured as the time from first dose to first use of rescue medication or dropout due to adverse event or lack of efficacy (*P<0.05 vs placebo; †P<0.05 vs IBU 250 mg; ‡P<0.05 vs APAP 650 mg).

Kaplan-Meier estimates for TMPR are shown in FIG. 8A. TMPR was significantly faster with all 3 active treatments compared with placebo (P<0.001). The TMPR with FDC IBU/APAP 250 mg/500 mg was 47.9 minutes and significantly faster than that observed for IBU 250 mg (65.9 minutes; P=0.003), APAP 650 mg (56.6 minutes; P=0.031), and placebo (not applicable [N/A]; P<0.001; Table 10).

Results for TFPR are shown in Table 11. All active treatment groups attained FPR significantly faster than placebo (P<0.001 for all comparisons), but there were no significant differences between active treatment groups (median TFPR: FDC IBU/APAP 250 mg/500 mg, 21.3 minutes; IBU 250 mg, 24.6 minutes; APAP 650 mg. 24.2 minutes).

All active treatment groups delivered significantly better pain relief than placebo for all comparisons in the 0-8 hour interval (TOTPAR$_{0-8}$; all, P<0.001) and the 6-8 hour interval (TOTPAR$_{6-8}$; all, P<0.001). In addition, FDC IBU/APAP 250 mg/500 mg provided superior pain relief relative to IBU 250 mg and APAP 650 mg alone for both the 0-8 hour interval (TOTPAR$_{0-8}$; P=0.002 and P<0.001, respectively) and the 6-8 hour interval (TOTPAR$_{6-8}$; P=0.013 and P<0.001, respectively).

FIG. 8B shows Kaplan-Meier estimates for duration of pain relief as measured by time to treatment failure. All active treatments were significantly superior to placebo (P<0.001; Table 12). The median duration of pain relief (as assessed using median time to treatment failure) was almost 10.5 hours for FDC IBU/APAP 250 mg/500 mg compared with 10.1 hours for IBU 250 mg alone, 7.5 hours for APAP 650 mg alone, and 1.8 hours for placebo. The duration of pain relief was significantly longer with the FDC than with placebo and APAP 650 mg alone (both P<0.001) but did not reach statistical significance versus IBU 250 mg alone (P=0.069).

The cumulative proportion of treatment failures after 8 hours was 69.6%, 24.4%, 33.1%, and 51.5% in the placebo, FDC IBU/APAP 250 mg/500 mg, IBU-alone, and APAP-alone groups, respectively. The FDC group had significantly fewer treatment failures than the placebo and APAP groups (P<0.001), but this difference was not significant compared with the IBU-alone group (P=0.064).

For the Patient Global Evaluation of study medication, all active treatment groups were significantly better than placebo (P<0.001 for all comparisons). In addition, the FDC IBU/APAP 250 mg/500 mg treatment group was significantly better than both IBU 250 mg (P=0.004) and APAP 650 mg (P<0.001) alone.

Efficacy: Multiple-Dose Study 3.

Figure 9:
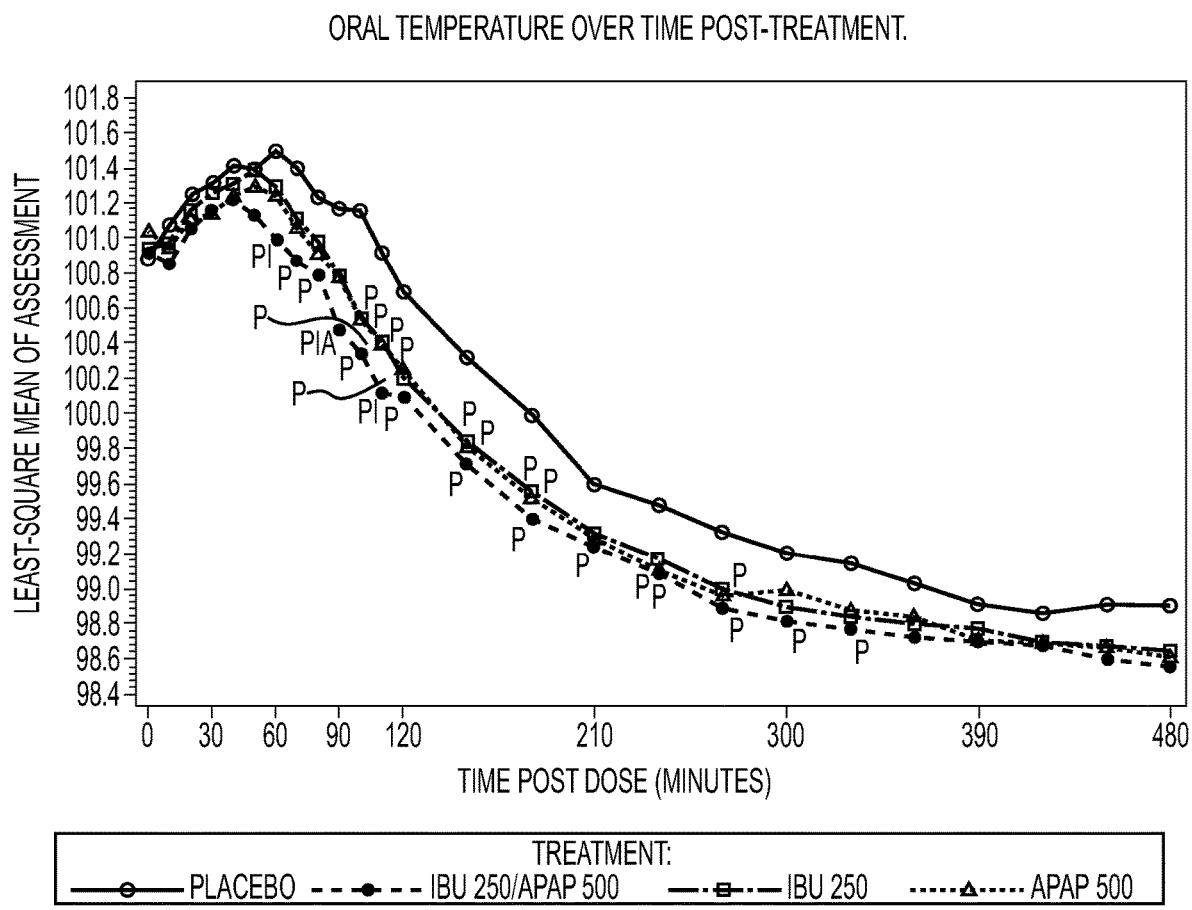
FIG. 9 shows mean oral temperature for each study arm post-treatment with the FDC (IBU 250 mg/APAP 500 mg); IBU 250 mg; APAP 500 mg; or placebo (Example 5).

FIG. 9 shows numerical pain intensity difference score over time in multiple-dose Study 3 (*P<0.05 vs placebo).

As shown in FIG. 9, FDC IBU/APAP 250 mg/500 mg was significantly superior to placebo at all time points studied for PID[11]. Study 3 met its primary endpoint: FDC IBU/APAP 250 mg/500 mg was significantly better than placebo for SPID[11]$_{0-24}$ (P<0.001; Table 9). FDC IBU/APAP 250 mg/500 mg was also significantly better than placebo over the SPID[11]$_{6-8}$ interval (P<0.001).

The median TMPR in this study was 59.2 minutes for FDC IBU/APAP 250 mg/500 mg compared with 165.9 minutes for placebo (P<0.001; Table 10). TFPR for the FDC IBU/APAP 250 mg/500 mg group (median: 28.2 minutes) was significantly faster than for the placebo group (N/A; P<0.001; Table 11). In total, 87.8% of patients taking FDC IBU/APAP 250 mg/500 mg attained FPR versus 29.3% of patients taking placebo.

For TOTPAR, the FDC delivered significantly better pain relief than placebo for all intervals assessed over 48 hours (P<0.001 for all interval comparisons).

A lower percentage of patients in the FDC/APAP 250 mg/500 mg group, 36.6%, took at least 1 dose of rescue medication (or was withdrawn early due to AE) between first dose and second dose, when compared with placebo (87.8%). The duration of relief was significantly longer for the FDC group when compared with the placebo group (median: 82.0 minutes; P<0.001; Table 12).

For the Patient Global Evaluation of study drug the FDC IBU/APAP 250 mg/500 mg treatment group was rated significantly better than placebo at both 24 and 48 hours postdose (P≤0.001 for both comparisons).

Studies 2 and 3—Safety.

The FDC IBU/APAP 250 mg/500 mg was generally well tolerated, and there were no unexpected AEs observed. In both studies, the most commonly reported AEs were nausea, vomiting. dizziness, and headache, all of which occurred more frequently in the placebo group than in the active treatment groups (Table 13). The incidence of these AEs was lowest for FDC IBU/APAP 250 mg/500 mg in both studies.

Studies 2 and 3—Discussion.

The studies described herein evaluating the efficacy and tolerability of a new FDC of IBU 250 mg/APAP 500 mg met their respective primary endpoints. The single-dose study demonstrated that FDC IBU/APAP 250 mg/500 mg provided significantly better analgesia over 0-8 hours than placebo, IBU 250 mg alone, and APAP 650 mg alone. In the multiple-dose study, FDC IBU/APAP 250 mg/500 mg was significantly better than placebo during all time periods studied, demonstrating that efficacy was sustained with multiple doses over 2 days with an 8-hour dosing interval. These results are consistent with previous studies on different FDCs of IBU and APAP. Earlier studies of an FDC of IBU/APAP 200 mg/500 mg demonstrated superior analgesic efficacy compared with placebo or either agent alone. In addition, Study I above found that FDC IBU/APAP 250 mg/500 mg provided similar efficacy to IBU 400 mg. Onset of pain relief, as assessed using TFPR and TMPR, is an additional important metric for evaluating analgesic efficacy in acute pain. TFPR was 21 and 28 minutes for the FDC in Studies 2 and 3, respectively, and numerically better than either IBU or APAP alone in Study 2. The TMPR of 48 and 59 minutes for the FDC in Studies 2 and 3 was consistent with the 39-74 minutes reported in previous studies of FDC IBU/APAP 200 mg/500 mg and for the FDC IBU/APAP 250 mg/500 mg in the pilot study (54 minutes). TMPR for the FDC in Study 2 was also significantly faster than for IBU or APAP alone. These data demonstrate that the FDC provides a rapid onset of pain relief that occurs within 1 hour, a crucial attribute for any analgesic used for acute pain.

The median duration of pain relief with the FDC was approximately 10.5 hours in the single-dose study and was greater than 8 hours in the multiple-dose study (data were censored for all patients at 8 hours when they took the second dose of study drug). This duration of pain relief was significantly longer with FDC IBU/APAP 250 mg/500 mg than the approximately 7.5 hours observed for APAP 650 mg in single-dose Study 1. The results of this study are again consistent with an earlier Study 1 that also reported median duration of pain relief of over 10 hours with this FDC. This longer duration of pain relief with the FDC compared with placebo and APAP 650 mg was further supported by the significantly better analgesia observed during the 6- to 8-hour interval as measured by SPID[11]$_{6-8}$ (P<0.001 for FDC vs APAP 650 mg and placebo). An 8-hour dosing interval was confirmed in the multiple-dose study in which the FDC demonstrated superior pain relief compared with placebo throughout the 2-day evaluation period and no loss of efficacy with an 8-hour dosing regimen. Taken together, these data indicate that the FDC of Ibu/APAP 250 mg/500 mg can be dosed at 8-hour intervals, i.e. 3 times daily, without loss of efficacy. This 8-hour dosing interval would compare to the 4-6 hour dosing interval for currently available single-entity IBU and APAP products.

AEs occurred most frequently in the placebo group. Nausea, vomiting and dizziness are fairly common occurrences after oral surgery and may be related to postsurgical pain and/or to the greater usage of opioid rescue medication in that group. The AE profile of the FDC was comparable to or better than those of the 2 components alone. There were no unexpected AEs seen with the combination, and the safety profile of the FDC was consistent with that seen in previous studies.

These studies demonstrate that FDC IBU/APAP 250 mg/500 mg is a more effective analgesic than the same dose of each agent alone and is well tolerated. Importantly, these studies also demonstrate a rapid onset of analgesia within 1 hour and sustained analgesia over an 8-hour dosing interval. The maximum total daily doses of IBU and APAP for the FDC (750 mg IBU/1500 mg APAP) are substantially lower than the recommended maximum daily dose of either component administered alone (1200 mg and 4000 mg respectively); therefore, FDC IBU/APAP 250 mg/500 mg would be expected to have a favorable safety profile. Hence, this FDC may provide consumers with another nonopioid pain relief option with lower exposure to both IBU and APAP compared with standard OTC dosing of either agent alone.

TABLE 9

Summary Values and Pairwise Comparisons of SPID[11]$_{0-8}$ (Study 2) and SPID[11]$_{0-24}$ (Study 3).

| | Study 2: SPID[11]$_{0-8}$ | | | | Study 3: SPID[11]$_{0-24}$ | |
|---|---|---|---|---|---|---|
| | Placebo (n = 56) | FDC IBU/APAP 250 mg/500 mg (n = 172) | IBU 250 mg (n = 175) | APAP 650 mg (n = 165) | Placebo (n = 41) | FDC IBU/APAP 250 mg/500 mg (n = 82) |
| Mean (SD) | 4.1 (19.0) | 34.3 (19.6) | 28.9 (20.5) | 19.4 (20.0) | −7.05 (54.53) | 64.58 (64.55) |
| Median | 0.0 | 37.3 | 30.5 | 16.8 | −16.00 | 67.25 |
| Range | −30.8, 57.8 | −14.8, 76.8 | −23.5, 70.5 | −23.0, 70.3 | −71.0, 161.8 | −44.8, 206.0 |
| LSM (SE)* | 4.3 (2.6) | 34.4 (1.5) | 28.7 (1.5) | 19.6 (1.6) | −8.13 (9.43) | 64.76 (6.68) |
| | | Pairwise Comparisons | | | | |
| Vs. placebo | — | 30.08 | 24.42 | 15.32 | — | 72.89 |
| Tx Diff† | — | 24.14, 36.02 | (18.50, 30.35) | (9.35, 21.29) | — | (50.08, 95.71) |
| 95% CI† | — | <0.001§ | <0.001§ | <0.001§ | — | <0.001§ |
| P‡ | | | | | | |
| Vs. IBU | — | 5.66 | — | — | — | — |
| Tx Diff† | — | (1.51, 9.80) | — | — | — | — |
| 95% CI† | — | 0.008§ | — | — | — | — |
| P‡ | | | | | | |
| Vs. APAP | — | 14.76 | — | — | — | — |
| Tx Diff† | — | (10.55, 18.97) | — | — | — | — |
| 95% CI† | — | <0.001§ | — | — | — | — |
| P‡ | | | | | | |
| IBU vs. APAP | — | — | 9.10 | — | — | — |
| Tx Diff† | — | — | (4.90, 13.31) | — | — | — |
| 95% CI† | — | — | <0.001§ | — | — | — |
| P‡ | | | | | | |

*P values from ANCOVA model with treatment, sex, baseline categorical PSR as classification variables and baseline numerical PSR as a continuous covariate for Studies 2 and 3.
†Treatment difference (first treatment − second treatment) and corresponding 95% CI were calculated based on LSM from the model in *.
‡First treatment significantly better than the second at the 0.05 level.

TABLE 10

Summary Values and Pairwise Comparisons of Time to
Onset of Meaningful Pain Relief (Studies 2 and 3).

|  | Study 2 | | | | Study 3 | |
| --- | --- | --- | --- | --- | --- | --- |
|  | Placebo (n = 56) | FDC IBU/APAP 250 mg/500 mg (n = 172) | IBU 250 mg (n = 175) | APAP 650 mg (n = 165) | Placebo (n = 41) | FDC IBU/APAP 250 mg/500 mg (n = 82) |
| Median (minutes)* | N/A | 47.9 | 65.9 | 56.6 | 165.9 | 59.2 |
| 95% CI (median)† | N/A | 41.6, 57.4 | 57.2, 81.6 | 50.5, 4.6 | 88.0, 170.0 | 47.7, 74.5 |
| Number(%) with event‡ | 16 (28.6) | 147 (85.5) | 139 (79.4) | 118 (71.5) | 10 (24.4) | 72 (87.8) |
| Pairwise Comparisons | | | | | | |
| Vs. placebo P value | — | <0.00§ | <0.001§ | <0.001§ | — | <0.001§ |
| Vs. IBU P value | — | 0.003§ | — | — | — | — |
| Vs. APAP P value | — | 0.031§ | — | — | — | — |
| IBU Vs. APAP P value | — | — | 0.631 | — | — | — |

*After first dose in Study 3.
†Using the method of Simon Rand Lee YJ, "Nonparametric confidence limits for survival probabilities and median survival time," *Cancer Treat Rep* 1982; 66: 37-42.
‡Number (%) of patients with meaningful relief.
§First treatment significantly better than the second at the 0.05 level.

TABLE 11

Summary Values and Pairwise Comparisons of Time to Onset
of First Perceptible Pain Relief (Studies 2 and 3).

|  | Study 2 | | | | Study 3 | |
| --- | --- | --- | --- | --- | --- | --- |
|  | Placebo (n = 56) | FDC IBU/APAP 250 mg/500 mg (n = 172) | IBU 250 mg (n = 175) | APAP 650 mg (n = 165) | Placebo (n = 41) | FDC IBU/APAP 250 mg/500 mg (n = 82) |
| Median (minutes)* | N/A | 21.3 | 24.6 | 24.2 | NIA | 28.2 |
| 95% CI (median)† | N/A | 18.7, 24.2 | 22.3. 27.8 | 20.7, 29.9 | NIA | 23.3, 29.7 |
| Number (%) with event‡ | 16 (28.6) | 149 (86.6) | 139 (79.4) | 118 (71.5) | 12 (29.3) | 72 (87.8) |
| Pairwise Comparisons | | | | | | |
| Vs. placebo P value | — | <0.001§ | <0.001§ | <0.001§ | — | <0.001§ |
| Vs. IBU P value | — | 0.088 | — | — | — | — |
| Vs. APAP P value | — | 0.133 | — | — | — | — |
| IBU Vs. APAP P value | — | — | 0.887 | — | — | — |

*After first dose in Study 3.
†Using the method of Simon Rand Lee YJ. Nonparametric confidence limits for survival probabilities and median survival time. *Cancer Treat Rep* 1982; 66: 37-42.
‡Number (%) of patients with meaningful relief.
§First treatment significantly better than the second at the 0.05 level.

TABLE 12

Summary Values and Pairwise Comparisons of Duration of Pain Relief (Studies 2 and 3).

| | Study 2 | | | | Study 3 | |
|---|---|---|---|---|---|---|
| | Placebo (n = 56) | FDC IBU/APAP 250 mg/500 mg (n = 172) | IBU 250 mg (n = 175) | APAP 650 mg (n = 165) | Placebo (n = 41) | FDC IBU/APAP 250 mg/500 mg (n = 82) |
| Median (minutes)* | 107.0 | 629.0 | 608.5 | 449.0 | 82.0 | N/A |
| 95% CI (median)† | 86.0, 173.0 | 570.0, 720.0 | 545.0, 671.0 | 399.0, 547.0 | 75.0, 99.0 | N/A |
| Number(%) with event‡ | 40 (71.4) | 96 (55.8) | 105 (60.0) | 105 (63.6) | 36 (87.8) | 30 (36.6) |
| | | Pairwise Comparisons | | | | |
| Vs. placebo P value | — | <0.001§ | <0.001§ | <0.001§ | — | <0.001§ |
| Vs. IBU P value | — | 0.069 | — | — | — | — |
| Vs. APAP P value | — | <0.001§ | — | — | — | — |
| IBU vs. APAP P value | — | — | 0.005§ | — | — | — |

*After first dose in Study 3.
†Using the method of Simon Rand Lee YJ, "Nonparametric confidence limits for survival, probabilities and median survival time," *Cancer Treat Rep* 1982; 66: 37-42.
‡Number (%) of patients with treatment failure.
§First treatment significantly better than the second at the 0.05 level.

TABLE 13

Summary of Treatment-Emergent Adverse Events Occurring in ≥2% of Patients in Any Treatment Group from the Single-Dose Study 2 and in Multiple-Dose Study 3.

| | Single-Dose Study 2 | | | | Multiple-Dose Study 3 | |
|---|---|---|---|---|---|---|
| Adverse event, n (%) | Placebo (n = 56) | FDC IBU/APAP 250 mg/500 mg (n = 172) | IBU 250 mg (n = 175) | APAP 650 mg (n = 165) | Placebo (n = 41)) | FDC IBU/APAP 250 mg/500 mg (n = 82) |
| Nausea | 17 (30.4) | 17 (9.9) | 24 (13.7) | 33 (20.0) | 8 (19.5) | 5 (6.1) |
| Vomiting | 11 (19.6) | 7 (4.1) | 15 (8.6) | 20 (12.1) | 6 (14.6) | 4 (4.9) |
| Dizziness | 4 (7.1) | 5 (2.9) | 6 (3.4) | 12 (7.3) | 4 (9.8) | 2 (2.4) |
| Headache | 0 | 0 | 3 (1.7) | 4 (2.4) | 4 (9.8) | 2 (2.4) |
| Flushing | 2 (3.6) | 0 | 2 (1.1) | 1 (0.6) | — | — |
| Vision blurred | | | | | 1 (2.4) | 0 |
| Abdominal pain | | | | | 1 (2.4) | 0 |
| Constipation | | | | | 1 (2.4) | 0 |
| Dyspepsia | | | | | 1 (2.4) | 0 |
| Sensitivity of the teeth | | | | | 1 (2.4) | 0 |
| Arthropod bite | | | | | 1 (2.4) | 0 |
| Cough | | | | | 1 (2.4) | 0 |
| Pruritis | | | | | 1 (2.4) | 0 |
| Swelling face | | | | | 1 (2.4) | 0 |
| Orthostatic hypotension | | | | | 1 (2.4) | 0 |

Example 5—Antipyretic Efficacy of the FDC in an Endotoxin-Induced Fever Model

Purpose:

This study evaluated the antipyretic efficacy, onset of effect and tolerability of a single dose of FDC IBU/APAP 250 mg/500 mg compared with placebo and each monocomponent at the same dose.

Methods:

This was a single-center, randomized, double-blind, placebo-controlled, full-factorial study in healthy males aged 18-55 years in whom pyrexia was induced by intravenous administration of a reference standard endotoxin (RSE). After RSE administration and attainment of an oral temperature ≥100.5° F. (38.1° C.), subjects were randomized 3:3:3:1 to receive a single oral dose of FDC IBU/APAP 250 mg/500 mg, APAP 500 mg, IBU 250 mg, or placebo in double-blind fashion. Oral temperature was subsequently measured every 10 minutes for the first 2 hours and then every 30 minutes until 8 hours post dose. Time-weighted sum of temperature differences from baseline to 8 hours ($WSTD_{0-8}$) after study medication administration was the primary efficacy endpoint. Secondary endpoints included WSTD scores from 0-2, 0-4, 0-6, and 6-8 hours; time to return to "normal" temperature; time to rescue medication use; global drug evaluation. Safety was monitored and assessed via adverse events (AEs).

Findings:

Two hundred ninety subjects were randomized; 273 were included in the primary efficacy analysis set. $WSTD_{0-8}$ was significantly better for FDC IBU/APAP 250 mg/500 mg (P=0.002), IBU 250 mg (P=0.030), and APAP 500 mg (P=0.023) versus placebo; there were no significant differences between active treatments. For $WSTD_{0-2}$, the FDC, but not its monocomponents, was statistically significant versus placebo (P=0.004).

All active treatments were significantly better (P<0.05) for $WSTD_{0-4}$ and $WSTD_{0-6}$ versus placebo; there were no differences in $WSTD_{6-8}$ between groups. Temperature returned to normal during the 8-hour treatment period in approximately 50% of subjects in each treatment group. Rescue medication was taken by only 1 subject (IBU group). Post hoc analyses of WSTD at early time points revealed significant treatment differences favoring FDC versus placebo and IBU for $WSTD_{50-110}$; for $WSTD_{80-110}$, FDC provided significant treatment differences versus placebo and both monocomponents. Overall, 223/290 (76.9%) subjects experienced AEs related to the RSE; only 2 subjects experienced treatment-related AEs (rash with FDC, ear pain with placebo).

Implications:

FDC IBU/APAP 250 mg/500 mg provide an effective antipyretic treatment option offering faster onset of antipyresis that lasted longer than the same doses of IBU and APAP alone.

Participants and Methods

Study Design.

This was a single-center, randomized, double-blind, placebo-controlled, full-factorial single-dose study in subjects in whom pyrexia was induced by intravenous (IV) administration of a reference standard endotoxin (RSE). In this standardized model, fever was induced by endotoxin (gram-negative bacterial lipopolysaccharide) derived from *Escherichia coli* O113, which was developed as a national biological reference standard in 1976 by the National Institute of Allergy and Infectious Diseases and the US Food and Drug Administration. The RSE used in this study was supplied by List Biological Laboratories, Inc. (Campbell, CA, USA).

Subject eligibility was determined at a screening visit within 28 days prior to study drug treatment; eligible subjects were assigned sequential subject numbers by the investigator. Subjects were healthy males aged 18-55 years, inclusive, with a normal, stable body temperature at screening and day 0, body mass index of 17.5-37.0 kg/m$^2$, and total body weight ≥50 kg at screening, demonstrably adequate veins for IV catheter insertion, and who were willing and able to comply with all study procedures. Subjects able to father children must have agreed to use a highly effective method of contraception throughout the study and for at least 28 days after the last dose of treatment. Female subjects were not enrolled due to potential teratogenicity concerns associated with the use of the RSE. Key exclusion criteria included: the presence or history of significant medical history or laboratory abnormalities that could have placed the subject at increased risk, including the presence or history of gastrointestinal disorders or excessive bleeding; a history of recurrent acute or chronic infections of any type or any findings suggestive of occult infection; cold or flu symptoms within 2 weeks prior to first administration of study treatment; screening supine blood pressure ≤90 or ≥140 mmHg (systolic) or ≤50 or ≥90 mmHg (diastolic) following at least 5 minutes of supine rest; screening supine 12-lead electrocardiogram (ECG) demonstrating corrected QT >450 msec or a QRS interval >120 msec at screening and on day 1; heart rate (HR) reduction to ≤50 beats per minute or deemed to be at high risk of syncope and/or hypotension per investigator judgment following carotid sinus massage; a positive urine drug screen or alcohol breath test during screening or on day 0; history of regular alcohol consumption; unwilling to abstain from tobacco or nicotine-containing products; treatment with an investigational drug within 30 days or 5 half-lives (whichever is longer) prior to the first dose of study medication; use of prescription, non-prescription, or dietary supplements within 7 days or 5 half-lives (whichever is longer); administration of endotoxin within 3 months; or history of sensitivity to heparin, or heparin-induced thrombocytopenia.

Subjects entered the study center on day 0 to confirm eligibility, i.e., afebrile state, defined as a mean oral temperature 97.4° F. to 98.8° F. not varying by more than 0.4° F. on 3 repeated measures over 30 minutes and still meeting inclusion/exclusion criteria. Subjects who remained eligible for the study remained in-house until after completion of all study procedures.

Subjects received prophylactic ondansetron, 8 mg intravenously, approximately 30 minutes prior to administration of the RSE to reduce the likelihood of nausea and vomiting. Prior to RSE administration, changes to prior treatments were recorded; blood pressure and HR were measured; and a 12-lead ECG was obtained. Oral temperatures were recorded, with "normal" for each subject being the temperature recorded immediately prior to RSE administration.

Assessments

Subject eligibility Subject assessments included physical examination, vital sign measurement, ECG evaluation, and laboratory studies (hematology, serum chemistry, urinalysis). The baseline oral temperature was defined as the temperature reading obtained immediately prior to administration of study medication, after the subject had reached an RSE-induced oral temperature ≥100.5° F. (38.1° C.) that was required for randomization. After randomization and study medication administration, oral temperature was measured using a standardized electronic digital thermometer every 10 minutes for the first 2 hours, and then every 30 minutes until 8 hours post dose. Subjects were assessed for emergence of AEs at each temperature evaluation time point. Respiratory rate and blood pressure were measured every hour, an ECG was performed after 8 hours, and subjects were discharged if appropriate. Clinic staff conducted a safety follow-up by calling all subjects within 24 hours after discharge and 14 days after the last dose of study medication.

Study Endpoints.

The primary efficacy endpoint was the time-weighted sum of temperature differences from baseline to 8 hours ($WSTD_{0-8}$), with weights being equal to the time elapsed between each 2 consecutive time points. Secondary endpoints included the weighted sum of temperature differences from baseline to 2 hours ($WSTD_{0-2}$), from baseline to 4 hours ($WSTD_{0-4}$), from baseline to 6 hours ($WSTD_{0-6}$), and from 6 to 8 hours ($WSTD_{6-8}$). The temperature difference from baseline at each post-dosing assessment was also evaluated, as well as the time to fever clearance as measured by the time to reach normal temperature (temperature immediately before administration of RSE) and time to administration of rescue medication. The proportion of subjects requiring rescue medication by 2, 3, 4, 5, 6, 7, and 8 hours was also reported. A global evaluation of study drug was performed at the end of the 8-hour study period or at the time of rescue administration by asking subjects, "How would you rate this medication as a fever reducer?" using a 6-point categorical scale ranging from 0 (very poor) to 5 (excellent). Safety and tolerability were monitored throughout the study via assessment of AEs, discontinuation due to AEs, serious AEs (SAES), vital signs, laboratory results, and ECG recordings.

A post hoc analysis was conducted to analyze FDC treatment effects on discrete WSTDs over early post-treatment time points where the FDC had demonstrated significantly superior effects over the monocomponents IBU and APAP. This analysis was carried out using an ANCOVA model with treatment term and covariates time from the first RSE full dose to randomization and baseline temperature. Two WSTD endpoints were analyzed: the WSTD from baseline during the 50-to-110 minute post-treatment window ($WSTD_{50-110\ min}$) using temperature values at 60, 70, 80, 90, 100, and 110 minutes; and the WSTD from baseline during the 80-to-110 minute post-treatment window ($WSTD_{80-110\ min}$) using temperature values at 90, 100, and 110 minutes.

Results.

Participants and Baseline Characteristics.

A total of 607 subjects were screened, and 290 were randomized. Of these, 273 subjects (94.1%) were included in the primary analysis (mITT) set for efficacy; 290 subjects comprised the safety set. In the safety analysis set, 21 of 23 subjects (including the 11 described above) who discontinued the study did so due to AEs related to the RSE. Baseline characteristics were well balanced between groups (Table 14). Per the study design, all of the subjects were male, as indicated. The majority of the study population (78.0%) were white and had a mean age of 32.2 years.

The mean time from administration of the full dose of RSE to randomization (i.e., oral temperature ≥100.5° F. [38.1° C.]) ranged from 124.3 to 140.4 minutes.

Efficacy

Primary Endpoint.

Figure 10:
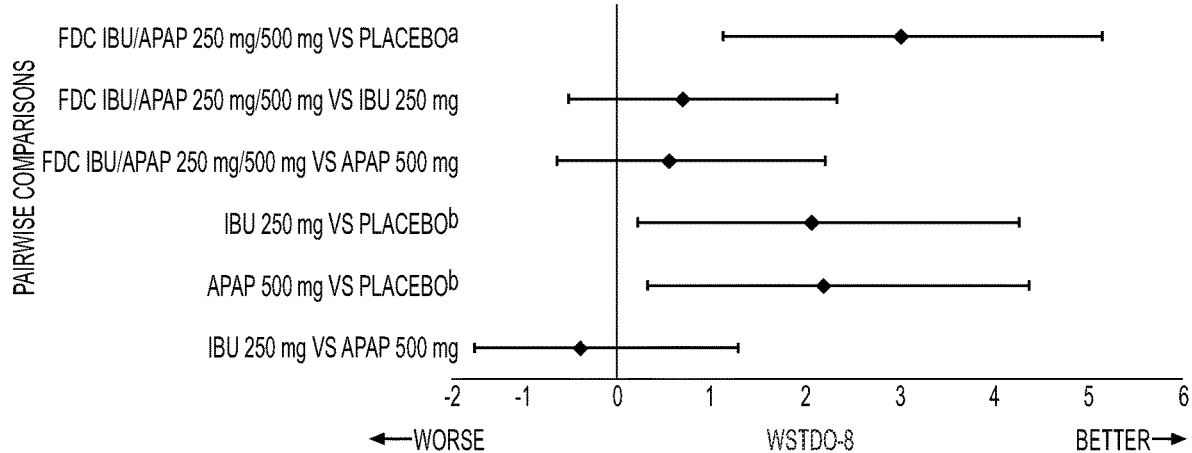
FIG. 10 depicts the time-weighted sum of temperature differences from baseline over 0-8 hours, calculated as treatment difference (first treatment minus second treatment) and 95% confidence intervals based on least-squares mean difference ($^a$P=0.002 vs placebo; $^b$P<0.05 vs placebo) (Example 5).

The mean oral temperature for each study arm over the course of the study is shown in FIG. 10. (LSM at baseline (0 point) calculated from ANCOVA model with treatment group term and covariate of time from the first RSE full dose to randomization. LSM at post-baseline calculated from ANCOVA model with treatment group term and covariates of time from first RSE full dose to randomization and baseline temperature. ($^a P \leq 0.05$ vs placebo; $^b P \leq 0.01$ vs placebo; $^c P \leq 0.001$ vs placebo; $^d P \leq 0.05$ vs IBU 250 mg; $^e P \leq 0.05$ vs APAP 500 mg). (P: significantly better than placebo at the 0.05 level; I: significantly better than IBU 250 mg at the 0.05 level; A: significantly better than APAP 650 mg at the 0.05 level).

For the primary efficacy parameter, the LSM (SE) $WSTD_{0-8}$ for the placebo, FDC, IBU 250 mg, and APAP 500 mg groups was 9.42 (0.89), 12.55 (0.51), 11.65 (0.51), and 11.77 (0.51), respectively. The difference between FDC and placebo was statistically significant (P=0.002); FDC was numerically but not statistically better than the IBU or APAP components (Table 15). Both the IBU 250 mg and APAP 500 mg doses were significantly better than placebo (P<0.05).

Secondary Endpoints.

Results for the WSTD at other time intervals are summarized in Table 15. The FDC was significantly better than placebo in the 0- to 2-hour interval ($WSTD_{0-2}$; P=0.004), but neither IBU or APAP separated from placebo. $WSTD_{0-4}$ and

TABLE 14

| | | Subject Demographics and Baseline Characteristics | | |
|---|---|---|---|---|
| | Placebo (n = 27) | FDC IBU/APAP 250 mg/500 mg (n = 81) | IBU 250 mg (n = 83) | APAP 500 mg (n = 82) |
| Mean age, years (SD) | 28.7 (8.2) | 33.2 (10.6) | 32.3 (10.4) | 32.3 (10.1) |
| | | Race, n (%) | | |
| White | 19 (70.4) | 67 (82.7) | 63 (75.9) | 64 (78.0) |
| Black or African American | 5 (18.5) | 9 (11.1) | 18 (21.7) | 12 (14.6) |
| Asian | 2 (7.4) | 1 (1.2) | 0 | 3 (3.7) |
| Other | 1 (3.7) | 4 (4.9) | 2 (2.4) | 3 (3.7) |
| | | Ethnicity, n (%) | | |
| Hispanic or Latino | 2 (7.4) | 4 (4.9) | 4 (4.8) | 3 (3.7) |
| Not Hispanic or Latino | 25 (92.6) | 77 (95.1) | 79 (95.2) | 79 (96.3) |
| BMI at screening, kg/m² (SD) | 27.13 (4.88) | 27.23 (4.19) | 27.83 (4.12) | 27.87 (3.84) |
| Mean time from RSE first full dose to randomization, min (SD) | 140.4 (53.7) | 138.5 (42.1) | 124.3 (40.6) | 132.0 (44.3) |
| Mean RSE total dosage, ng (SD) | 231.0 (58.0) | 238.0 (51.4) | 232.9 (57.1) | 237.8 (54.4) |
| Mean baseline temperature, ° F. (SD) | 100.87 (0.27) | 100.91 (0.36) | 100.95 (0.41) | 101.05 (0.53) |

$WSTD_{0-6}$ showed similar patterns to the primary endpoint, with the FDC, IBU 250 mg, and APAP 500 mg all being significantly better than placebo. $WSTD_{6-8}$ showed no differences between any of the groups and placebo.

TABLE 15

Summary of Time-Weighed Sum of Temperature Differences From Baseline.

| | Placebo (n = 27) | FDC IBU/APAP 250 mg/500 mg (n = 81) | IBU 250 mg (n = 83) | APAP 500 mg (n = 82) |
|---|---|---|---|---|
| Primary and Secondary WSTD Endpoints. | | | | |
| $WSTD_{0-8\,h}{}^a$ | | | | |
| Mean (SD) | 9.28 (6.39) | 12.54 (5.52) | 11.09 (6.35) | 12.39 (6.28) |
| LSM (SE) | 9.42 (0.89) | 12.55 (0.51) | 11.65 (0.51) | 11.77 (0.51) |
| $WSTD_{0-2\,h}$ | | | | |
| Mean (SD) | −0.42 (1.83) | 0.48 (1.83) | −0.19 (1.86) | 0.21 (1.73) |
| LSM (SE) | −0.50 (0.27) | 0.40 (0.16) | 0.01 (0.15) | 0.10 (0.15) |
| $WSTD_{0-4\,h}$ | | | | |
| Mean (SD) | 1.79 (3.44) | 3.69 (3.15) | 2.61 (3.34) | 3.41 (3.17) |
| LSM (SE) | 1.72 (0.45) | 3.60 (0.26) | 2.98 (0.26) | 3.14 (0.26) |
| $WSTD_{0-6\,h}$ | | | | |
| Mean (SD) | 5.26 (4.83) | 7.95 (4.24) | 6.65 (4.79) | 7.65 (4.60) |
| LSM (SE) | 5.29 (0.64) | 7.91 (0.37) | 7.12 (0.37) | 7.21 (0.37) |
| $WSTD_{6-8\,h}$ | | | | |
| Mean (SD) | 4.96 (2.23) | 5.69 (1.90) | 5.49 (2.26) | 5.84 (2.33) |
| LSM (SE) | 5.09 (0.36) | 5.76 (0.21) | 5.60 (0.20) | 5.61 (0.20) |

Pairwise Treatment Comparisons.

| | FDC IBU/APAP 250 mg/500 mg Vs. Placebo | FDC IBU/APAP 250 mg/500 mg Vs. IBU 250 mg | FDC IBU/APAP 250 mg/500 mg Vs. APAP 500 mg | IBU 250 mg Vs. Placebo | APAP 500 mg Vs. Placebo | IBU 250 mg Vs. APAP 500 mg |
|---|---|---|---|---|---|---|
| $WSTD_{0-8\,h}{}^a$ | | | | | | |
| Treatment difference (95% CI) | 3.14 (1.13, 5.15) | 0.91 (−0.52, 2.33) | 0.79 (−0.64, 2.21) | 2.23 (0.22, 4.25) | 2.35 (0.33, 4.37) | −0.12 (−1.54, 1.29) |
| P value | .002[b] | .210 | .280 | .030[b] | .023[b] | .864 |
| $WSTD_{0-2\,h}$ | | | | | | |
| Treatment difference (95% CI) | 0.90 (0.29, 1.51) | 0.39 (−0.04, 0.82) | 0.30 (−0.13, 0.74) | 0.51 (−0.10, 1.13) | 0.60 (−0.01, 1.21) | −0.09 (−0.52, 0.34) |
| P value | .004[b] | .078 | .172 | .098 | .054 | .692 |
| $WSTD_{0-4\,h}$ | | | | | | |
| Treatment difference (95% CI) | 1.87 (0.86, 2.88) | 0.61 (−0.10, 1.33) | 0.45 (−0.27, 1.17) | 1.26 (0.24, 2.27) | 1.42 (0.40, 2.44) | −0.16 (−0.87, 0.55) |
| P value | <.001[b] | .094 | .217 | .015[b] | .006[b] | .659 |
| $WSTD_{0-6\,h}$ | | | | | | |
| Treatment difference (95% CI) | 2.62 (1.16, 4.08) | 0.79 (−0.25, 1.82) | 0.70 (−0.34, 1.74) | 1.83 (0.37, 3.29) | 1.92 (0.45, 3.39) | −0.09 (−1.12, 0.94) |
| P value | <.001[b] | .135 | .186 | .014[b] | .011[b] | .865 |
| $WSTD_{6-8\,h}$ | | | | | | |
| Treatment difference (95% CI) | 0.67 (−0.13, 1.48) | 0.16 (−0.41, 0.73) | 0.15 (−0.43, 0.72) | 0.51 (−0.29, 1.32) | 0.53 (−0.28, 1.34) | −0.01 (−0.58, 0.55) |
| P value | .101 | .582 | .614 | .212 | .202 | .965 |

[a] Primary efficacy endpoint.
[b] First treatment significantly better than the second at 0.05 level.

The FDC was significantly better than placebo in the 0- to 2-hour interval (WSTD$_{0-2}$; P=0.004), but neither IBU or APAP separated from placebo. WSTD$_{0-4}$ and WSTD$_{0-6}$ showed similar patterns to the primary endpoint, with the FDC, IBU 250 mg, and APAP 500 mg all being significantly better than placebo. WSTD$_{6-8}$ showed no differences between any of the groups and placebo.

Other Evaluations.

In an analysis of temperature changes at different time points during the study, the FDC significantly reduced subjects' temperatures versus placebo beginning 60 minutes after treatment administration. The differences versus placebo remained significant at each subsequent assessment through 5.5 hours (P<0.05 for each assessment). In contrast, significant temperature reductions were noted with IBU 250 mg versus placebo at 100 and 110 minutes and 2, 2.5, and 3 hours (P<0.05 for each) and with APAP 500 mg at 100 and 110 minutes and 2, 2.5, 3, 4, and 4.5 hours. Endotoxin-induced fever was significantly reduced with the FDC versus IBU 250 mg at 60, 90, and 110 minutes and with the FDC versus APAP 500 mg at 90 minutes.

Figure 11:
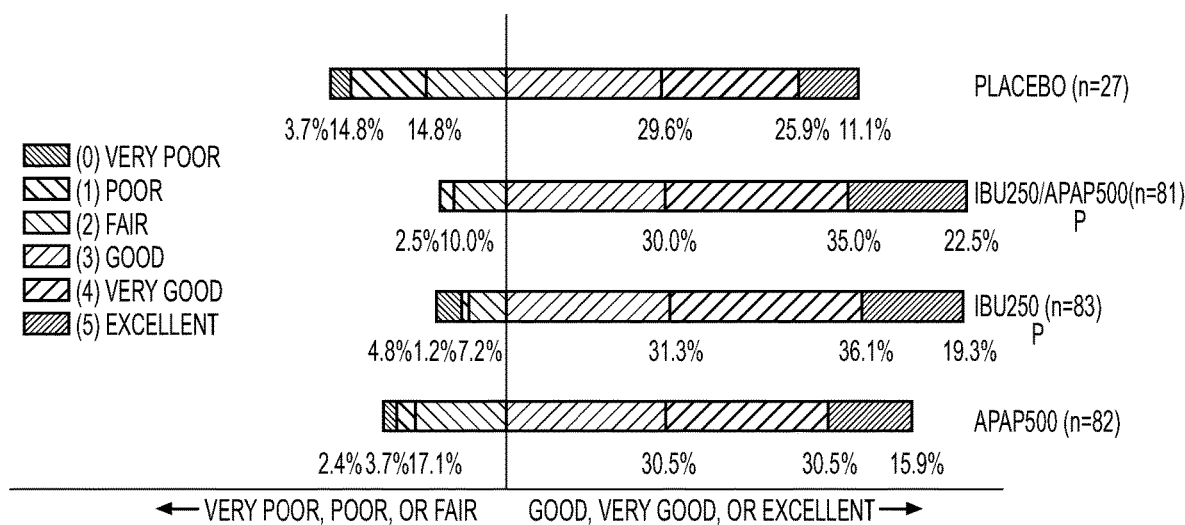
FIG. 11 depicts global evaluation of FDC IBU 250 mg/APAP 500 mg, with $^a$P<0.05 vs placebo from ANCOVA model when analyzed as a continuous variable, with treatment group term and time from the first RSE full dose to randomization and baseline temperature as covariates; and $^b$P=0.05 vs placebo on Chi square test when analyzed as a categorical variable. Results are presented as percentages (Example 5).

For the a priori Global Evaluation of study medication, subjects were asked to rate the study medication on a 6-point scale from 0-5 (where 0=very poor to 5=excellent) in response to the question, "How would you rate this medication as a fever reducer?" In FIG. 11, results are presented as percentages. [a]P<0.05 vs placebo from ANCOVA model when analyzed as a continuous variable, with treatment group term and time from the first RSE full dose to randomization and baseline temperature as covariates; [b]P=0.05 vs placebo on Chi square test when analyzed as a categorical variable.

The majority of subjects in all arms rated their study medication as being a "good" or "very good" fever reducer. In the Chi square analysis, IBU 250 mg was rated significantly higher than placebo (P=0.050). In the ANCOVA analysis, both the FDC and IBU 250 mg treatment groups, but not the APAP 500 mg group, rated their treatment significantly higher than those in the placebo group (P<0.05 for each).

Post Hoc WSTD Analyses.

In an effort to identify early time intervals (between 0 to 2 hours) when the FDC demonstrated statistical superiority over the monocomponents, a post hoc analysis was conducted to determine the WSTD between treatment groups for time intervals of 50-110 minutes and 80-110 minutes post-baseline. Results from that analysis are presented in Table 16.

TABLE 16

Summary of Time-Weighed Sum of Temperature Differences From Baseline: Post Hoc Analysis of Early Time Points.

| | Placebo (n = 27) | FDC IBU/APAP 250 mg/500 mg (n = 81) | IBU 250 mg (n = 83) | APAP 500 mg (n = 82) |
|---|---|---|---|---|
| | | Early Time Point Analysis (post hoc) | | |
| | | WSTD$_{50\text{-}110\ min}$ | | |
| Mean (SD) | −0.22 (1.088) | 0.41 (1.019) | −0.02 (1.094) | 0.19 (1.023) |
| LSM (SE) | −0.271 (0.15) | 0.361 (0.09) | 0.103 (0.09) | 0.135 (0.09) |
| | | WSTD$_{80\text{-}110\ min}$ | | |
| Mean (SD) | −0.04 (0.559) | 0.34 (0.490) | 0.13 (0.586) | 0.23 (0.540) |
| LSM (SE) | −0.061 (0.08) | 0.323 (0.05) | 0.190 (0.05) | 0.192 (0.05) |

| | Pairwise Treatment Comparisons | | | | | |
|---|---|---|---|---|---|---|
| | FDC IBU/APAP 250 mg/500 mg Vs. Placebo | FDC IBU/APAP 250 mg/500 mg Vs. IBU 250 mg | FDC IBU/APAP 250 mg/500 mg Vs APAP 500 mg | IBU 250 mg Vs. Placebo | APAP 500 mg Vs. Placebo | IBU 250 mg Vs. APAP 500 mg |
| | | | WSTD$_{50\text{-}110\ min}$ | | | |
| Treatment difference (95% CI) | 0.632 (0.28, 0.98) | 0.258 (0.01, 0.51) | 0.226 (−0.02, 0.48) | 0.374 (0.02, 0.73) | 0.406 (0.05, 0.76) | −0.032 (−0.28, 0.22) |
| P value | <.001[a] | .042[a] | .076 | .037[a] | .024[a] | .801 |
| | | | WSTD$_{80\text{-}110\ min}$ | | | |
| Treatment difference (95% CI) | 0.383 (0.20, 0.57) | 0.133 (0.00, 0.26) | 0.131 (0.00, 0.26) | 0.251 (0.07, 0.43) | 0.253 (0.07, 0.44) | −0.002 (−0.13, 0.13) |
| P value | <.001[a] | .045[a] | .049[a] | .008[a] | .007[a] | .972 |

[a]First treatment significantly better than the second at 0.05 level.

As shown in the table, the FDC provided a statistically significant treatment difference in WSTD$_{50\text{-}110\ min}$ compared with placebo (P<0.001) and IBU (P=0.042); a trend toward significance was found for FDC versus APAP (P=0.076). For the 80-110 minute post-baseline comparison, FDC was statistically superior to placebo (P<0.001), IBU (P=0.045), and APAP (P=0.049).

Safety and Tolerability

Treatment-Emergent AEs (TEAEs) During Endotoxin Administration Period.

A total of 290 subjects (100%) reported a TEAE due to RSE during the RSE administration period. The most common of these AEs were chills in 281 (96.9%) subjects and tremors in 236 (81.4%) subjects; these AEs were generally similar across treatment groups. Other TEAEs included headache in 181 (62.4%), pain in 117 (40.3%), HR increased in 80 (27.6%), nausea in 66 (22.8%), malaise in 49 (16.9%), and myalgia in 35 (12.1%); these were reported in similar percentages across treatment groups. Only one subject (0.3%) reported a TEAE not due to RSE during the RSE administration period (IBU 250 mg group, infusion-related reaction).

TEAEs During Study Drug Treatment Period.

A total of 223 of 290 subjects (76.9%) reported AEs considered related to RSE during the study drug treatment period. The most common of these AEs were increased HR in 129 (44.5%), pyrexia in 100 (34.5%), hypotension in 62 (21.4%), nausea in 32 (11.0%), and headache in 31 (10.7%); none were serious. Pyrexia was reported by a higher percentage of subjects in the placebo and IBU 250 mg treatment groups (41.4% in each group) than with the FDC or APAP 500 mg (29.9% in each). Nausea and headache due to RSE, reported by 32 (11.0%) and 31 (10.7%) subjects, respectively, were also reported in a higher percentage of participants treated with placebo (20.7% and 24.1%, respectively) and IBU 250 mg (12.6% and 14.9%, respectively), when compared with the FDC (8.0% and 6.9% respectively) and APAP 500 mg (9.2% and 5.7%, respectively) treatment groups. A total of 21 (7.2%) of 290 subjects reported TEAEs due to RSE (vomiting and pyrexia) that led to withdrawal from the study (4 [13.8%], 6 [6.9%], 5 [5.7%], and 6 [6.9%] subjects in the placebo, FDC, IBU, and APAP treatment groups, respectively).

Discussion.

This trial demonstrated the statistical superiority of a single oral dose of FDC IBU/APAP 250 mg/500 mg as compared with placebo on the primary endpoint of $WSTD_{0-8}$, thereby confirming efficacy of the FDC as an antipyretic. IBU 250 mg and APAP 500 mg alone were also statistically superior to placebo on this outcome.

Although the FDC did not show statistical significance for the primary endpoint compared with individual monocomponents alone, it did show a numerical advantage over the individual monocomponents.

For the secondary endpoint of $WSTD_{0-2}$, the FDC, but not IBU 250 mg or APAP 500 mg, was statistically superior to placebo. Additional analysis found that FDC treatment significantly reduced subjects' temperatures relative to placebo from 60 minutes to 5.5 hours post dose, compared with 100 minutes to 3 hours for IBU 250 mg and 100 minutes to 4.5 hours for APAP 500 mg. A post hoc analysis assessing discrete, early WSTD time intervals showed that the FDC was superior to IBU 250 mg between 50 and 110 minutes and superior to both IBU and APAP between 80 and 110 minutes.

Taken together with previous studies of combined IBU and APAP in children (see Malya R R, "Does combination treatment with ibuprofen and acetaminophen improve fever control?," *Ann Emerg Med.* 2013; 61:569-570; Paul I M et al., "Efficacy of standard doses of ibuprofen alone, alternating, and combined with acetaminophen for the treatment of febrile children," *Clin Ther.* 2010; 32:2433-2440; and Purssell E, "Systematic review of studies comparing combined treatment with paracetamol and ibuprofen, with either drug alone," *Arch Dis Child.* 2011; 96:1175-1179), these results suggest that the FDC has a faster onset of antipyresis, is more effective at reducing fever, and has a longer duration of action than either monocomponent.

An induced-fever model was used to assess the antipyretic activity of the FDC IBU/APAP 250 mg/500 mg in this study (see Suffredini AF and Noveck R J, "Human endotoxin administration as an experimental model in drug development," *Clin Pharmacol Ther.* 2014; 96:418-422). Use of an RSE provides for a fever that can be reproduced in a clinical setting for study purposes. Indeed, the RSE was developed by the National Institute of Allergy and Infectious Diseases and the US Food and Drug Administration specifically to aid pharmaceutical manufacturers and biomedical researchers in standardizing study design. While a naturalistic fever study may be preferred, there are a number of logistical barriers to conducting such a study, foremost of which is recruiting adult subjects with a fever, since the individual is more likely to self-treat than to report for enrollment in a clinical trial. Other challenges include seasonal variation in the incidence and severity of viral and bacterial infections, as well as the fact that subjects would likely be at different stages of their illness when randomized to treatment and have different source illnesses. All of these factors could confound the results and/or increase the number of subjects required for the study due to increased variability.

A limitation to this study is that the more conservative approach used for the administration of the RSE batch, which appeared more potent than those used in previous studies as evidenced by the frequency and earlier onset of RSE-related adverse events, may have resulted in a lower and shorter duration of fever that was not sustained over the 8-hour post-treatment observation period, as evidenced by the fact that 51.9% of subjects in the placebo arm returned to a normal temperature during the observation period. This, in turn, may have limited model sensitivity regarding observation of a statistical separation of active treatments from placebo (downside sensitivity) as well as statistical separation of the active treatments from each other (upside sensitivity). Due to the restrictive criteria used for study entry, these results may not be generalizable to febrile patients with medical comorbidities, those younger than 18 or older than 55 years of age, and to females. Nevertheless, the data indicate that the FDC is an efficacious antipyretic that provides faster fever reduction than the same doses of the individual components.

The majority of AEs reported in this trial were attributed to the RSE. All of these events were mild to moderate in intensity. Overall, the FDC formulation was shown to be safe and generally well tolerated in otherwise healthy subjects with an induced fever, with no new safety concerns for the FDC identified in this study.

Conclusions.

This study demonstrated that an FDC of IBU 250 mg/APAP 500 mg reduced fever significantly better than placebo over 0-8 hours. In addition, the FDC was numerically better over this period than both monocomponents, but did not reach statistical significance for this primary endpoint; a similar trend was observed across the majority of pre-defined efficacy endpoints. The FDC was statistically significantly superior to placebo over 0-2 hours, while IBU and APAP alone were not, suggesting that the FDC may provide a faster onset of antipyresis. This conclusion is supported by results of post hoc analyses that showed that FDC was superior to IBU 250 mg between 50 and 110 minutes and was superior to both IBU 250 mg and APAP 500 mg between 80 and 110 minutes. There was a very low incidence of TEAEs in this study, indicating that the FDC was safe and generally well tolerated. FDC IBU/APAP 250 mg/500 mg may provide another effective treatment option for fever with a more rapid onset and a longer duration than with comparable doses of IBU and APAP monocomponents.

Thus, the FDC and each monocomponent provided superior fever reduction to placebo. In induced fever, faster and longer antipyresis occurred with FDC vs monotherapies.

| ABBREVIATIONS | |
|---|---|
| AE | Adverse event |
| ANCOVA | Analysis of covariance |
| APAP | Acetaminophen |
| BMI | Body mass index |
| CI | Confidence interval |
| COX | Cyclooxygenase |
| Diff | Difference |
| ECG | Electrocardiogram |
| FDC | Fixed dose combination |
| H | Hour |
| HR | Heart rate |
| IBU | Ibuprofen |
| IV | Intravenous |
| LSM | Least squares mean |
| mITT | Modified intent-to-treat |
| N/A | Not applicable |
| NMDA | N-methyl-D-aspartate |
| NR | Not reached |
| RSE | Reference standard endotoxin |
| SAE | Serious AE |
| SD | Standard deviation |
| SE | Standard error |
| PID[11] | Pain intensity difference based on 11-point numerical pain severity rating scale |
| PSR | Pain severity rating |
| SD | Standard deviation |
| SE | Standard error |
| $SPID[11]_{0-8}$ | Time-weighted sum of PID scores based on the 11-point numerical pain severity rating scale during the interval from baseline to 8 hours |
| $SPID[11]_{0-8/0-24}$ | Time-weighted sum of pain intensity differences over 8 or 24 hours |
| TEAE | treatment-emergent adverse event |
| TOTPAR | Time-weighted sum of pain relief rating scores |
| $TOTPAR_{0-2}$ | Time-weighted sum of pain relief rating scores over 0-2 hours |
| $TOTPAR_{0-6}$ | Time-weighted sum of pain relief rating scores over 0-6 hours |
| $TOTPAR_{0-8}$ | Time-weighted sum of pain relief rating scores over 0-8 hours |
| $TOTPAR_{0-8}$ | Time-weighted sum of pain relief rating scores over 0-8 hours |
| $TOTPAR_{0-12}$ | Time-weighted sum of pain relief rating scores over 0-12 hours |
| Tx | Treatment |
| Vs. | Versus |
| WSTD | Weighted sum of temperature difference |
| $WSTD_{0-2}$ | Weighted sum of temperature differences from baseline to 2 hours |
| $WSTD_{0-4}$ | Weighted sum of temperature differences from baseline to 4 hours |
| $WSTD_{0-6}$ | Weighted sum of temperature differences from baseline to 6 hours |
| $WSTD_{0-8}$ | Weighted sum of temperature differences from baseline to 8 hours |
| $WSTD_{6-8}$ | Weighted sum of temperature differences from 6 to 8 hours |
| $WSTD_{50-110}$ | Weighted sum of temperature differences from baseline during the 50-to-110 minute post-treatment window |
| $WSTD_{80-110}$ | Weighted sum of temperature differences from baseline during the 80-to-110 minute post-treatment window |

We claim:

1. An oral tablet comprising:
   active pharmaceutical ingredients ibuprofen and acetaminophen, wherein the ibuprofen is present in an amount of 100 to 300 mg and acetaminophen is present in an amount of 150 to 600 mg, wherein the ratio of ibuprofen to acetaminophen is 1:3 to 1:1 by weight; and
   wherein the tablet further comprises intragranular and extragranular components,
   wherein the intragranular component comprises the active ingredients, a binding agent, a disintegrating agent and a glidant; and the extragranular components comprise a disintegrating agent, a glidant and a lubricant,
   said tablet being essentially free of unmodified starch, and wherein pregelatinized starch and hypromellose are the sole intragranular binding agents.

2. The oral tablet according to claim 1 comprising:
   (i) the active ingredients present intragranularly;
   (ii) 5% to 20% by weight pregelatinized starch present intragranularly;
   (iii) 0.5% to 2.5% by weight Hypromellose present intragranularly;
   (iv) 0.5% to 3% by weight of glyceryl dibehenate present extragranularly;
   (v) 1% to 10% by weight croscarmellose present intragranularly and extragranularly; and
   (vi) 1% to 5% by weight colloidal silicon dioxide present intragranularly and extragranularly.

3. The oral tablet according to claim 1 comprising:
   (i) the active ingredients present intragranularly;
   (ii) 8% to 15% by weight pregelatinized starch, present intragranularly;
   (iii) 1% to 2% by weight Hypromellose, present intragranularly;
   (iv) 1% to 2% by weight of glyceryl dibehenate, present extragranularly;
   (v) 5% to 8% by weight croscarmellose, present intragranularly and extragranularly; and
   (vi) 2% to 4% by weight colloidal silicon dioxide, present intragranularly and extragranularly.

4. The oral tablet according to claim 2 or 3 wherein the ibuprofen is present in an amount of 125 mg and acetaminophen in an amount of 250 mg; or the ibuprofen is present in an amount of 250 mg and acetaminophen in an amount of 500 mg.

5. The oral tablet according to claim 1 wherein the pregelatinized starch is present in an amount from 4% to 25% by weight.

6. The oral tablet according to claim 1 wherein the Hypromellose is present in an amount from 1% to 2% by weight.

7. The oral tablet according to claim 1 wherein pregelatinized starch is present as a first binding agent in an amount ranging from 8 to 15% by weight and Hypromellose is present as a second binding agent in an amount from 1% to 2% by weight.

8. The oral tablet according to claim 1 wherein the weight ratio of pregelatinized starch to Hypromellose is about 7:1 to about 12:1.

9. The oral tablet according to claim 1 wherein the disintegrant comprises a super disintegrant present intragranularly, extragranularly or both intragranularly and extragranularly.

10. The oral tablet according to claim 1 wherein the super disintegrant is present both intragranularly and extragranularly.

11. The oral tablet according to claim 9 or 10 wherein the super disintegrant is a cross-linked carboxymethyl cellulose.

12. The oral tablet according to claim 10 wherein the super disintegrant is present intragranularly in an amount from 0.5% to 5% by weight, and present extragranularly in an amount from 0.5% to 5% by weight.

13. The oral tablet according to claim 1 wherein the glidant comprises colloidal silicon dioxide.

14. The oral tablet according to claim 13 wherein the colloidal silicon dioxide is present intragranularly in an amount from 0.5% to 2% by weight and present extragranularly in an amount from 0.5% to 2% by weight.

15. The oral tablet according to claim 1 wherein the lubricant comprises glyceryl behenate.

16. The oral tablet according to claim 15 wherein the glyceryl behenate is present extragranularly in an amount from 0.5% to 2% by weight.

17. The oral tablet according to claim 1 where the intragranular component is present as a population of granules having a d50 of about 100 to about 200.

18. The oral tablet according to claim 1 wherein ibuprofen is present in an amount of 110 mg to 140 mg, and acetaminophen, in an amount of 230 mg to 270 mg.

19. The oral tablet according to claim 18 wherein ibuprofen is present in an amount of 125 mg and acetaminophen, in an amount of 250 mg.

20. The oral tablet according to claim 1 wherein ibuprofen is present in an amount of 250 mg and acetaminophen, in an amount of 500 mg.

21. A method for treating a mammalian subject in need thereof to relieve pain and/or inflammation, comprising orally administering to the subject the oral tablet of claim 1, said administration being optionally repeated at intervals of 8 hours until the subject attains relief from pain and/or inflammation.

22. A method for treating fever in a mammalian subject in need thereof, comprising orally administering to the subject an anti-pyretic composition comprising the oral tablet of claim 1, said administration being optionally repeated until the subject attains relief from fever.

23. The method according to claim 22 wherein the method provides a statistically significant faster onset of action over 0-2 hours relative to placebo.

24. A process for the preparing of an oral tablet according to claim 1 comprising the steps of preparing a granulate, admixing the granulate with any desired extragranular component to form a master blend, and compressing the master blend into the oral tablet.

* * * * *